(12) United States Patent
Liu et al.

(10) Patent No.: US 9,265,788 B2
(45) Date of Patent: Feb. 23, 2016

(54) COMPOSITIONS AND METHODS FOR TREATMENT OF MITOCHONDRIAL DISEASES

(71) Applicant: The Board of Trustees of the Leland Stanford Junior University, Palo Alto, CA (US)

(72) Inventors: Song Liu, Stanford, CA (US); Bingwei Lu, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 29 days.

(21) Appl. No.: 14/188,281

(22) Filed: Feb. 24, 2014

(65) Prior Publication Data

US 2014/0256786 A1    Sep. 11, 2014

Related U.S. Application Data

(60) Provisional application No. 61/769,372, filed on Feb. 26, 2013.

(51) Int. Cl.
*A61K 48/00* (2006.01)
*A61K 31/713* (2006.01)
*A61K 45/06* (2006.01)
*A61K 31/13* (2006.01)
*A61K 31/198* (2006.01)

(52) U.S. Cl.
CPC .............. *A61K 31/713* (2013.01); *A61K 31/13* (2013.01); *A61K 31/198* (2013.01); *A61K 45/06* (2013.01)

(58) Field of Classification Search
None
See application file for complete search history.

(56) References Cited

U.S. PATENT DOCUMENTS

| | | |
|---|---|---|
| 2002/0049176 A1 | 4/2002 | Anderson |
| 2005/0261217 A1 | 11/2005 | Dobie |
| 2011/0064722 A1 | 3/2011 | Lindquist |
| 2011/0159592 A1 | 6/2011 | You |
| 2012/0277286 A1 | 11/2012 | Youle |
| 2012/0294956 A1 | 11/2012 | Qian |

FOREIGN PATENT DOCUMENTS

WO    2012/158624    11/2012

OTHER PUBLICATIONS

Bingwei. "Mitochondrial Dynamics and Neurodegeneration" Current Neurology and Neuroscience Reports (May 2009), 9(3):212-219.

Brickley. "Trafficking kinesin protein (TRAK)-mediated transport of mitochondria in axons of hippocampal neurons" Movement Disorders (Aug. 2004), 19(8):978-81.

Chan. "Broad activation of the ubiquitin-proteasome system by Parkin is critical for mitophagy." Human Molecular Genetics (May 2011), 20(9):1726-37.

Chu. "A pivotal role for PINK1 and autophagy in mitochondrial quality control: implications for Parkinson disease" Human Molecular Genetics (Apr. 2010), 19(R1):R28-37.

Clark. "Drosophila pink1 is required for mitochondrial function and interacts genetically with parkin" Nature (Jun. 2006), 441(7097):1162-6.

Deng. "The Parkinson's disease genes pink1 and parkin promote mitochondrial fission and/or inhibit fusion in *Drosophila*" Proceedings of the National Academy of Sciences of the United States of America (Sep. 2008), 105(38):14503-8.

Dimauro. "Mitochondrial respiratory-chain diseases" The New England Journal of Medicine (Jun. 2003), 348 (26):2656-68.

D'Souza. "Arginine/Serine-rich Protein Interaction Domain-dependent Modulation of a Tau Exon 10 Splicing Enhancer: altered interactions and mechanisms for functionally antagonistic FTDP-17 mutations Delta280K and N279K" The Journal of Biological Chemistry (Feb. 2006) 281(5):2460-9.

Duncan. "The genetics of axonal transport and axonal transport disorders" PLoS Genetics (Sep. 2006), 2(9):e124.

Ebneth. "Overexpression of tau protein inhibits kinesin-dependent trafficking of vesicles, mitochondria, and endoplasmic reticulum: implications for Alzheimer's disease" The Journal of Cell Biology (Nov. 1998), 143(3):777-94.

Exner. "Loss-of-function of human PINK1 results in mitochondrial pathology and can be rescued by parkin" The Journal of Neuroscience: the official journal of the Society of Neuroscience (Nov. 2007), 27(45):12413-8.

Fatimathas. "LRRK2 gene key to Parkinson's Disease, say experts" Biology News (Aug. 2010), pp. 3.

Fransson. "Atypical Rho GTPases have roles in mitochondrial homeostasis and apoptosis" The Journal of Biological Chemistry (Feb. 2003), 278(8):64995-502.

Garcia-Rodriguez. "Puf3p, a Pumillio family RNA binding protein, localizes to mitochondria and regulates mitochondrial biogenesis and motility in budding yeast" The Journal of Cell Biology (Jan. 2007), 176(2):197-207.

Gautier. "Loss of PINK1 causes mitochondrial functional defects and increased sensitivity to oxidative stress" Proceeding of the National Academy of Sciences of the United States of America (Aug. 2008), 105(32):11364-9.

(Continued)

*Primary Examiner* — Kimberly Chong
(74) *Attorney, Agent, or Firm* — Bozicevic, Field & Francis LLP; David C. Scherer

(57) ABSTRACT

Methods and compositions are provided for the treatment of a mitochondrial disease in an individual with the mitochondrial disease. Aspects of the methods include administering an inhibitor of a mitochondrial transport protein to a subject having a mitochondrial disease. Also provided are reagents and kits for practicing the subject methods.

12 Claims, 17 Drawing Sheets
(6 of 17 Drawing Sheet(s) Filed in Color)

(56) References Cited

OTHER PUBLICATIONS

Gehrke. "Pathogenic LRRK2 negatively regulates microRNA-mediated translational repression" Nature (Jul. 2010), 466(7306):637-41.
Guo. "The GTPase dMiro is required for axonal transport of mitochondria to *Drosophila* synapses" Neuron (Aug. 2005), 47(3):379-93.
Imai. "Mitochondrial dynamics and mitophagy in Parkinson's disease: disordered cellular power plant becomes a big deal in a major movement disorder" Current Opinion in Neurobiology (Dec. 2011), 21(6):935-41.
Imai. "The loss of PGAM5 suppresses the mitochondrial degeneration caused by inactivation of PINK1 in *Drosophila*" PLoS Genetics (Dec. 2010), 6(12):e1001229.
Kim-Han. "The parkinsonian mimetic, MPP+, specifically impairs mitochondrial transport in dopamine axons" The Journal of Neuroscience: the official journal of the Society of Neuroscience (May 2011), 31(19):7212-21.
Lee. "Phosphorylation of kinesin in vivo correlates with organelle association and neurite outgrowth" The Journal of Biological Chemistry (Mar. 1995), 270(10):5600-5.
Liu. "Reduction of protein translation and activation of autophagy protect against PINK1 pathogenesis in *Drosophila melanogaster*" PLoS Genetics (Dec. 2010), 6(12):e1001237.
Liu. "Parkinson's disease-associated kinase PINK1 regulates Miro protein level and axonal transport of mitochondria" PLoS Genetics (2012), 8(3):e1002537.
Lu. "*Drosophila* models of neurodegenerative diseases" Annual Review of Pathology (2009), 4:315-42.
Magrane. "Mitochondrial function, morphology, and axonal transport in amyotrophic lateral sclerosis" Antioxidants & Redox Signaling (Jul. 2009), 11(7):1615-26.
Mai. "Decreased expression of Drp1 and Fis1 mediates mitochondrial elongation in senescent cells and enhances resistance to oxidative stress through PINK1" Journal of Cell Science (Mar. 15), 123(Pt 6):917-26.
Matsuda. "PINK1 stabilized by mitochondrial depolarization recruits Parkin to damaged mitochondria and activates latent Parkin for mitophagy" The Journal of Cell Biology (Apr. 2010), 189(2):211-21.
Misko. "Mitofusin 2 is necessary for transport of axonal mitochondria and interacts with the Miro/Milton complex" The Journal of Neuroscience: The Official Journal of the Society for Neuroscience (Mar. 2010), 30(12):4232-40.
Narendra. "Parkin is recruited selectively to impaired mitochondria and promotes their autophagy" The Journal of Cell Biology (Dec. 2008), 183(5):795-803.
Park. "Mitochondrial dysfunction in *Drosophila* PINK1 mutants is complemented by parkin" Nature (Jun. 2006), 441 (7097):1157-61.
Pilling. "Kinesin-1 and Dynein are the primary motors for fast transport of mitochondria in *Drosophila* motor axons" Molecular Biology of the Cell (Apr. 2006), 17(4):2057-68.
Pridgeon. "PINK1 protects against oxidative stress by phosphorylating mitochondrial chaperone TRAP1" PLoS Biology (Jul. 2007), 5(7):e172.
Qi. "A novel Drp1 inhibitor diminishes aberrant mitochondrial fission and neurotoxicity" Journal of Cell Science (Feb. 2013), 126(Pt 3):789-802.
Sato. "Genetic mutations and mitochondrial toxins shed new light on the pathogenesis of Parkinson's disease" Parkinson's Disease (2011), 2011:979231.
Schwartz. "Derivation, Enrichment, and characterization of Dopaminergic Nuerons from Pluripotent Stem Cells" Thesis for Doctoral Degree, Department of Medical Biochemistry and Biophysics, Karolinska Institutet, Stockholm, Sweden (2010), 90 Pgs.
Sterky. "Impaired mitochondrial transport and Parkin-independent degeneration of respiratory chain-deficient dopamine neurons in vivo" Proceedings of the National Academy of Sciences of the United States of America (Aug. 2011), 108(31):12937-42.
Stowers. "Axonal transport of mitochondria to synapses depends on milton, a novel *Drosophila* protein" Neuron (Dec. 2002), 36(6):1063-77.
Suen. "Parkin overexpression selects against a deleterious mtDNA mutation in heteroplasmic cybrid cells" Proceedings of the National Academy of Sciences of the United States of America (Jun. 2010), 107(26):11835-40.
Suzuki. "A serine protease, HtrA2, is released from the mitochondria and interacts with XIAP, inducing cell death" Molecular Cell (Sep. 2001), 8(3):613-21.
Swistowski. "Efficient Generation of Functional Dopaminergic Neurons from Human Induced Pluripotent Stem Cells Under Defined Conditions," Stem Cells (Oct. 2010), 28:1893-1904.
Tassin. "Chromosome 6-linked autosomal recessive early-onset Parkinsonism: linkage in European and Algerian families, extension of the clinical spectrum, and evidence of a small homozygous deletion in one family. The French Parkinson's Disease Genetics Study Group, and the European Consortium on Genetic Susceptibility in Parkinson's Disease" American Journal of Human Genetics (Jul. 1998), 63(1):88-94.
Valente. "Hereditary early-onset Parkinson's disease caused by mutations in PINK1" Science (May 2004), 304 (5674):1158-60.
Wang. "Antioxidants protect PINK1-dependent dopaminergic neurons in *Drosophila*" Proceedings of the National Academy of Sciences of the United States of America (Sep. 2006), 103(36):13520-5.
Wang. "PINK1 and Parkin target Miro for phosphorylation and degradation to arrest mitochondrial motility" Cell (Nov. 2011), 147(4):893-906.
Yang. "Pink1 regulates mitochondrial dynamics through interaction with the fission/fusion machinery" Proceedings of the National Academy of Sciences of the United States of America (May 2008), 105(19):7070-5.
Yang. "Mitochondrial pathology and muscle and dopaminergic neuron degeneration caused by inactivation of *Drosophila* Pink1 is rescued by Parkin" Proceedings of the National Academy of Sciences of the United States of America (Jul. 2006), 103(28):10793-8.
Yin. "Ventral Mesencephalon-Enriched Genes That Regulate the Development of Dopaminergic Neurons In Vivo" The Journal of Neuroscience (Apr. 2009), 29:5170-5182.
Yoshii. "Parkin mediates proteasome-dependent protein degradation and rupture of the outer mitochondrial membrane" The Journal of Biological Chemistry (Jun. 2011), 286(22):19630-40.
Yu. "The PINK1/Parkin pathway regulates mitochondrial dynamics and function in mammalian hippocampal and dopaminergic neurons" Human Molecular Genetics (Aug. 2011), 20(16):3227-40.
Zuchner. "Mechanisms of disease: a molecular genetic update on hereditary axonal neuropathies" Nature Clinical Practice. Neurology (Jan. 2006), 2(1):45-53.

Figure 3A-B
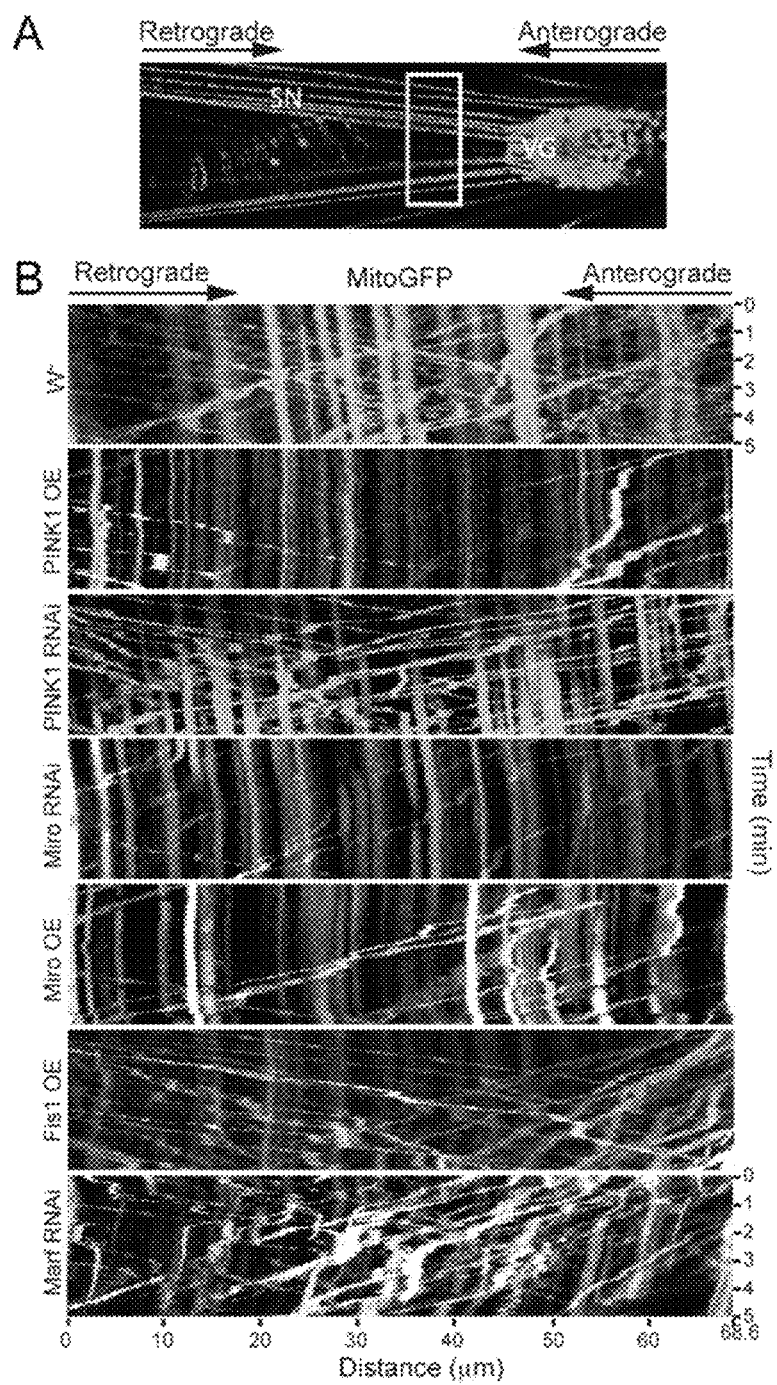

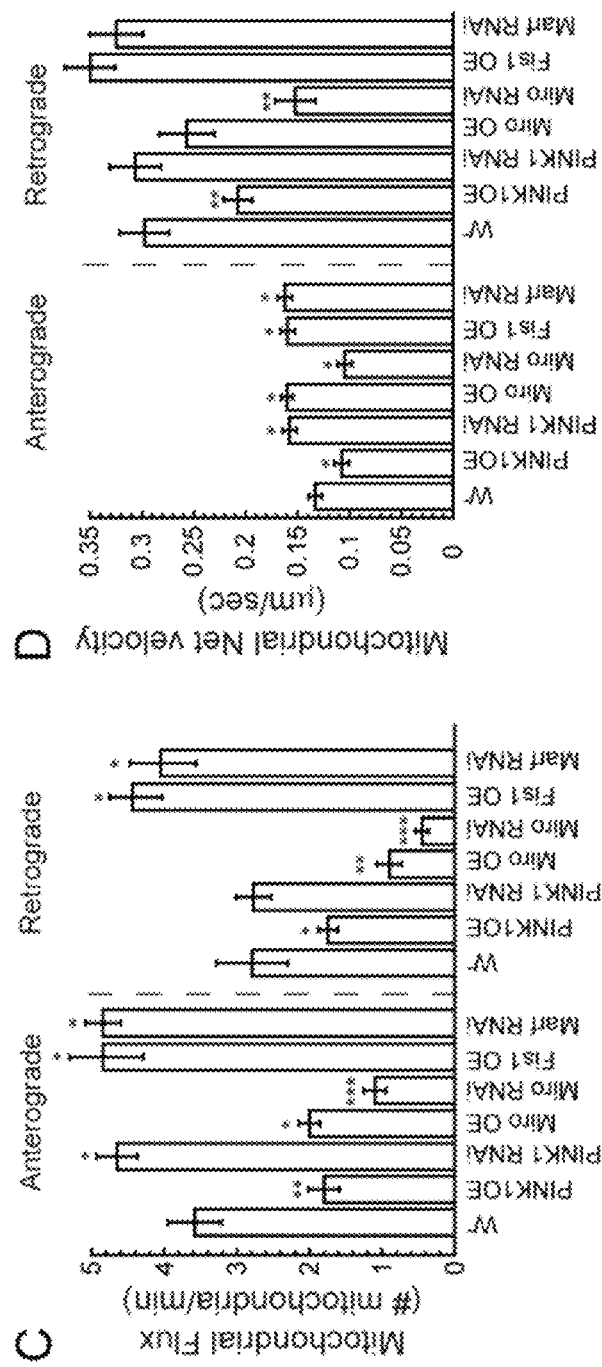
Figure 3C-D

Figure 3E-F
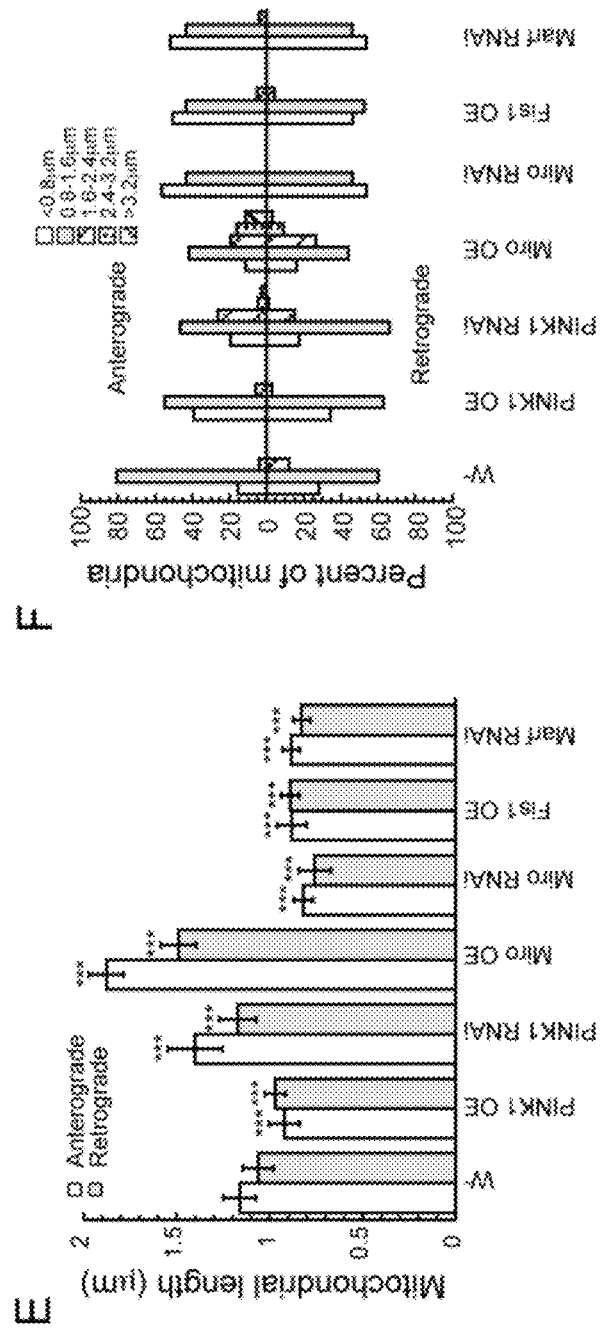

Figure 5C-E
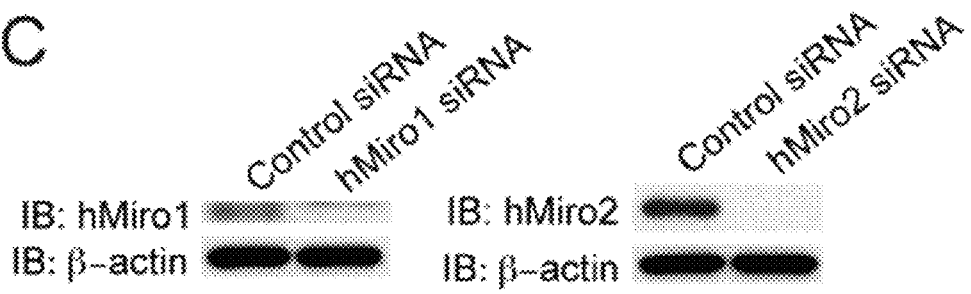
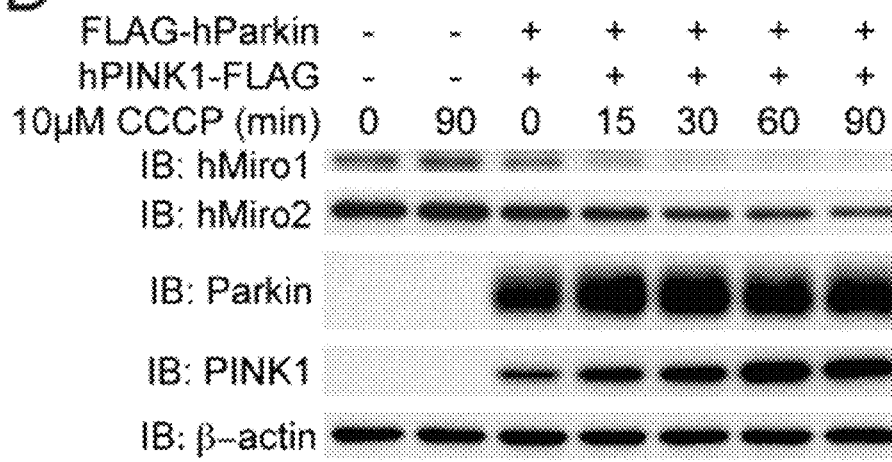
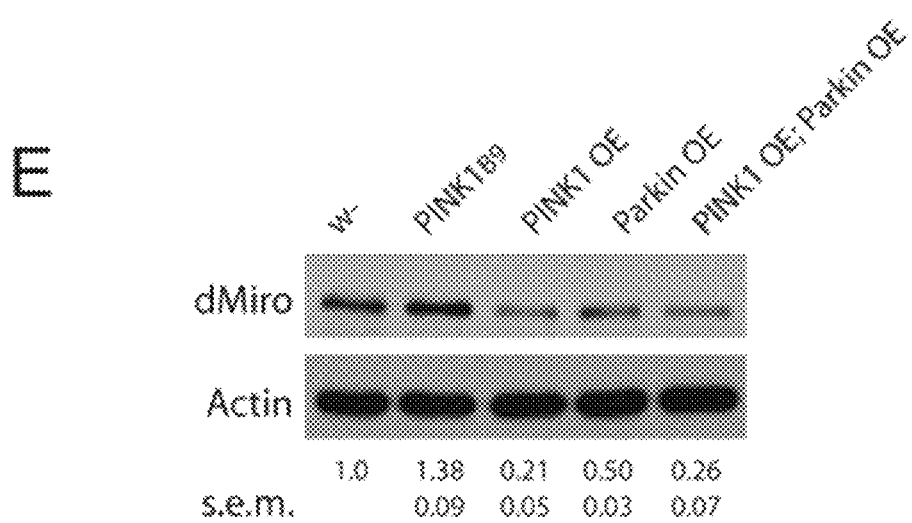

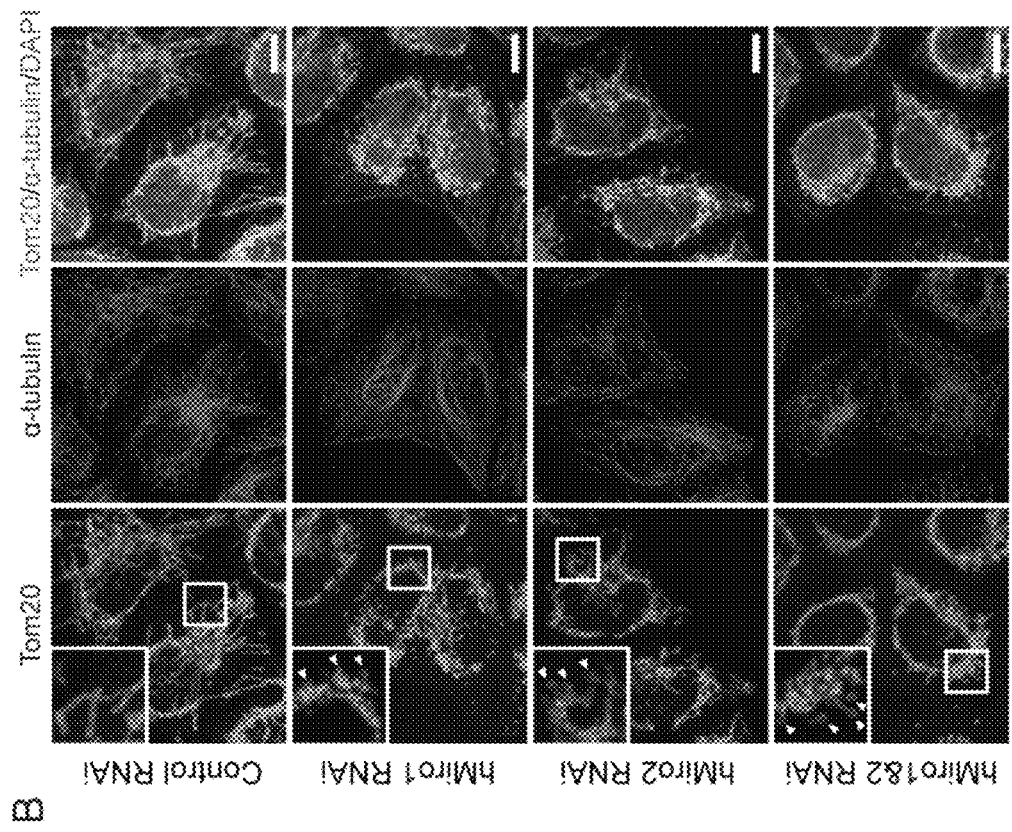

COMPOSITIONS AND METHODS FOR TREATMENT OF MITOCHONDRIAL DISEASES

CROSS REFERENCE TO RELATED APPLICATIONS

Pursuant to 35 U.S.C. §119 (e), this application claims priority to the filing date of the U.S. Provisional Patent Application Ser. No. 61/769,372 filed Feb. 26, 2013; the full disclosure of which is herein incorporated by reference.

GOVERNMENT RIGHTS

This invention was made with Government support under contract AR054926 awarded by the National Institutes of Health. The Government has certain rights in this invention.

FIELD OF THE INVENTION

Provided herein are compositions and method for the treatment of mitochondrial diseases in a subject.

BACKGROUND

Mitochondrial dysfunction can result in a host of debilitating mitochondrial diseases or disorders characterized by poor growth, loss of muscle coordination, muscle weakness, visual problems, hearing problems, learning disabilities, heart disease, liver disease, kidney disease, gastrointestinal disorders, respiratory disorders, neurological problems, autonomic dysfunction, and/or dementia. In many instances, these mitochondrial diseases are caused by acquired or inherited mutations in mitochondrial DNA or in nuclear genes that code for mitochondrial components or for cellular components that act as quality control checkpoints of mitochondrial function. For example, the mitochondrial disease Parkinson's disease (PD) is a common neurodegenerative movement disorder affecting 1% of the population above the age of 60 that has been linked to acquired or spontaneous mutations in mitochondrial genes or nuclear genes relevant to mitochondrial function. PD is characterized by the preferential loss and degeneration of dopaminergic neurons of the substantia nigra (SN) pars compacta and formation of Lewy bodies. PD patients exhibit resting tremor, bradykinesia, muscle rigidity and postural instability.

Although research is ongoing, treatment options are currently limited; vitamins are frequently prescribed, though the evidence for their effectiveness is limited. Rescuing dysfunctional mitochondria provides one approach for treating mitochondrial diseases or disorders. Membrane penetrating antioxidants and pyruvate are two examples of treatment options for improving mitochondrial dysfunction. As such, there is a need for the development of new therapeutic agents and methods for the treatment of mitochondrial disease.

SUMMARY

Methods and compositions are provided for the treatment of a mitochondrial disease in an individual with the mitochondrial disease. Aspects of the methods include administering an inhibitor of a mitochondrial transport protein to a subject having a mitochondrial disease. Also provided are reagents and kits for practicing the subject methods.

In one aspect, provided herein is a method of treating mitochondrial disease in a subject having a mitochondrial disease. In some embodiments the method includes the step of administering a therapeutically effective amount of an inhibitor of a mitochondrial transport protein to the subject. In some embodiments, the mitochondrial transport protein is a Miro protein (e.g., Miro1 or Miro2). In some embodiments, the mitochondrial transport protein is a trafficking kinesin (TRAK) protein (e.g., TRAK1 or TRAK2). In some embodiments, the mitochondrial transport protein is kinesin heavy chain (Khc).

In certain embodiments, the inhibitor of a mitochondrial transport protein is an antibody or fragment thereof. In other embodiments, the inhibitor is a polypeptide or peptide fragment, e.g. a dominant negative polypeptide. In other embodiments, the inhibitor is a small molecule. In yet other embodiments, the inhibitor is a nucleic acid. In particular embodiments, the nucleic acid inhibitor is a Miro-specific siRNA, a TRAK-specific siRNA, or a Khc-specific siRNA.

In certain embodiments, the mitochondrial disease is Parkinson's Disease (PD). In some such embodiments, the PD is a familial form of PD, e.g. a PTEN-induced putative kinase 1 (PINK-1)-associated form of PD, a Parkin-associated form of PD, an LRRK2-associated form of PD, an alpha-Synuclein (SNCA)-associated form of PD, a ubiquitin carboxy-terminal hydrolase L1 (UCHL1)-associated form of PD, a parkinson protein 7 (PARK7, DJ-1) associated form of PD, an ATP13A2-associated form of PD, a phospholipase A2, group VI (PLA2G6)-associated form of PD, a DnaJ (Hsp40) homolog, subfamily C, member 6 (DNAJC6, PARK19)-associated form of PD; a eukaryotic translation initiation factor 4 gamma, 1 (EIF4G1, PARK18)-associated form of PD; a F-box protein 7 (FBXO7)-associated form of PD; a GRB10 interacting GYF protein 2 (GIGYF2)-associated form of PD; a HtrA serine peptidase 2 (HTRA2)-associated form of PD; a synaptojanin 1 (SYNJ1)-associated form of PD; and a vacuolar protein sorting 35 homolog (VPS35)-associated form of PD. In other such embodiments, the PD is a sporadic form of Parkinson's Disease, for example, it is associated with a sporadic mutation in one of the aforementioned genes. In certain such embodiments, the subject inhibitor(s) is administered to the midbrain and/or putamen of the subject.

In some embodiments, the method further comprises the step of administering a therapeutically effective amount of one or more additional therapeutics for the treatment of the mitochondrial disease. In some embodiments, the additional therapeutic agent is selected from the group consisting of levodopa, a dopamine agonist, a MAO-B inhibitor, amantadine, an anticholinergic, a PUM1 antagonist, an SR protein antagonist, a Parkin agonist, a PINK1 agonist, an 4E-BP1 agonist, a Drp1 agonist, an Atg1 agonist, a TauS2A agonist, a Rbf1 agonist, a Dp antagonist, an E2f1 antagonist, a Polo-like kinase 2 antagonist and a Notch agonist. In some embodiments, the subject inhibitor(s) are provided at the same time as the additional therapeutic. In some embodiments, the subject inhibitor(s) are provided before the additional therapeutic. In some embodiments, the subject inhibitor(s) are provide after the additional therapeutic.

In another aspect, provided herein is a pharmaceutical composition comprising a mitochondrial transport protein inhibitor and a pharmaceutically acceptable carrier, which finds use in the treatment of a mitochondrial disease. In certain embodiments, the mitochondrial transport protein is a Miro protein (e.g., Miro1 or Miro2). In other embodiments, the mitochondrial transport protein is a TRAK protein (e.g., TRAK1 or TRAK2). In yet other embodiments, the mitochondrial transport protein is kinesin heavy chain (Khc).

In another aspect, provided herein are method for screening a candidate agent for activity in treating a mitochondrial disease in an individual. In some embodiments, the methods include contacting a cell with a candidate agent; and comparing a mitochondria-associated parameter to the mitochondria-associated parameter in cells that were not contacted with said candidate agent; wherein a change in the mitochondria-associated parameter indicates that the candidate agent will treat the mitochondrial disease in the individual. In some such embodiments, the mitochondria-associated parameter is selected from the group consisting of phosphorylation or ubiquitination of a Miro protein; phosphorylation or ubiquitination of a TRAK protein; phosphorylation or ubiquitination of khc; mitochondria transport rate; mitochondria length; and miro-TRAK-khc complex formation. In some embodiments, the cell comprises a gene mutation associated with a mitochondrial disease. In some embodiments, the mitochondrial disease is Parkinson's Disease. In some such embodiments, the gene mutation is a mutation in a gene selected from the group consisting of PTEN-induced putative kinase 1 (PINK-1); Parkin (also known as RBR E3 ubiquitin protein ligase, or PARK2); leucine-rich repeat kinase 2 (LRRK2); alpha-Synuclein (SNCA, PARK4); ubiquitin carboxy-terminal hydrolase L1 (UCHL1); parkinson protein 7 (PARK7, DJ-1); ATPase type 13A2 (ATP13A2); phospholipase A2, group VI (PLA2G6); DnaJ (Hsp40) homolog, subfamily C, member 6 (DNAJC6, PARK19); eukaryotic translation initiation factor 4 gamma, 1 (EIF4G1, PARK18); F-box protein 7 (FBXO7); GRB10 interacting GYF protein 2 (GIGYF2); HtrA serine peptidase 2 (HTRA2); synaptojanin 1 (SYNJ1); and vacuolar protein sorting 35 homolog (VPS35).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 3. PINK1 regulates mitochondrial motility in *Drosophila* larval motor neurons. (A) An image of a third instar larva expressing mitoGFP in the motor neurons. For time-lapse imaging, mitochondrial movement in segmental nerves (SN) was recorded near the ventral ganglion (VG) (indicated by the white box). (B) Representative kymographs of mitochondrial movement in the different genetic backgrounds. Each panel is a kymograph representation of the position of fluorescently labeled mitochondria as a function of time. Anterograde mitochondrial movements have positive slopes, whereas retrograde mitochondrial movements have negative slopes. Stationary mitochondria appear as vertical streaks. (C, D) Mitochondrial flux (C) and net velocity (D) in different genetic backgrounds. (E, F) Average mitochondrial length (E) and mitochondrial length distribution (F) in the various genetic backgrounds. Data are presented as mean±s.e.m.

DETAILED DESCRIPTION OF THE INVENTION

Figure 1:
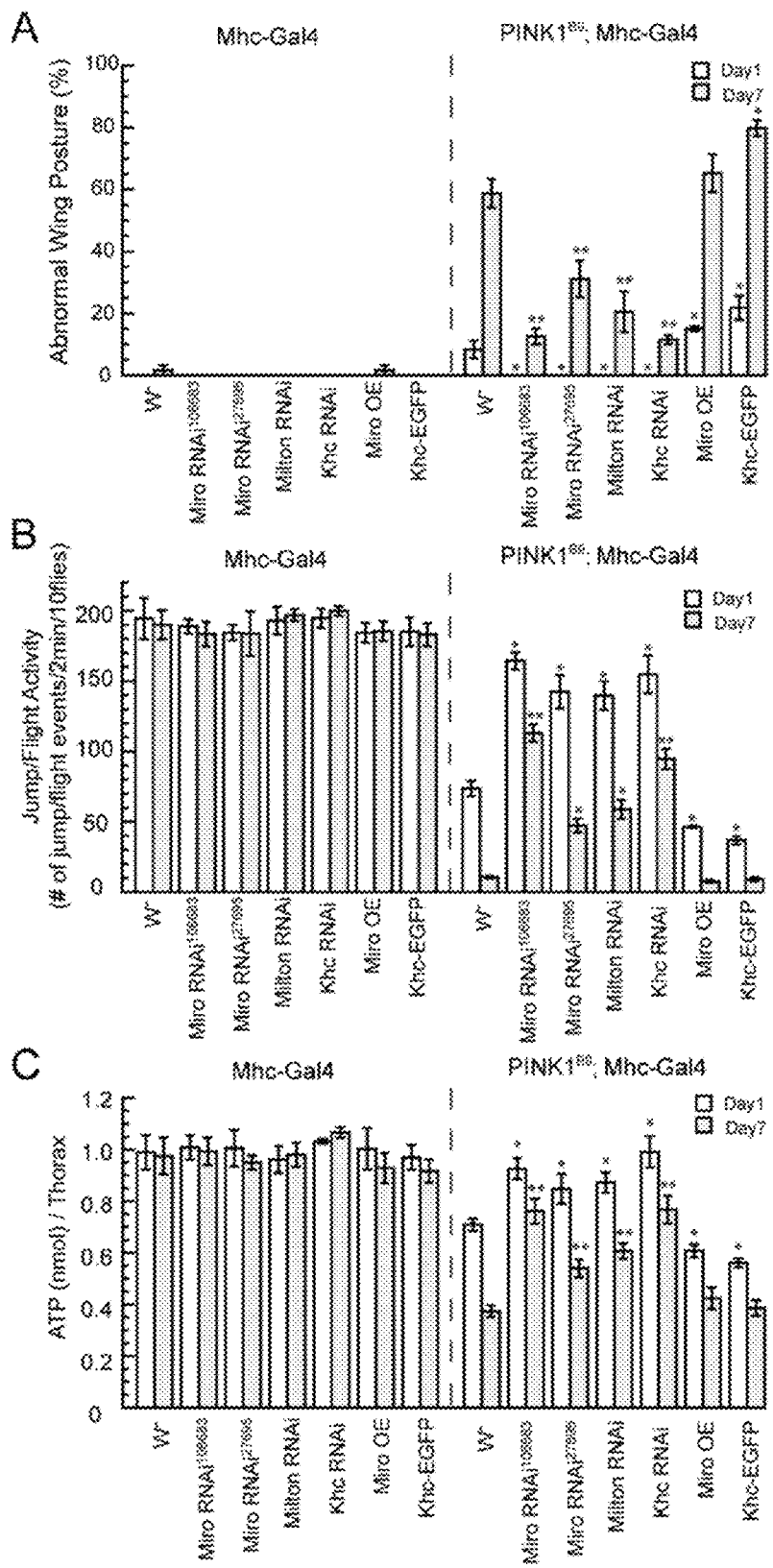
FIG. 1. Genetic interaction between PINK1 and the mitochondrial transport machinery in the muscle. Effects of knockdown or overexpression of Miro, Milton or Khc on the abnormal wing posture (A), jump/fly ability (B), and thoracic ATP level (C) of PINK1$^{B9}$ mutant are shown. Male flies of the corresponding genotypes were scored at 1-day or 7-day of age at 25° C. Miro-RNAi$^{106683}$ was used for the rest of studies. Data are from three independent experiments and the results are presented as mean±s.e.m.

Methods and compositions are provided for the treatment of a mitochondrial disease in an individual with the mitochondrial disease. Aspects of the methods include administering an inhibitor of a mitochondrial transport protein to a subject having a mitochondrial disease. Also provided are reagents and kits for practicing the subject methods. These and other objects, advantages and features of the invention will become apparent to those persons skilled in the art upon reading the details of the compositions and methods as more fully described below.

Before the present methods and compositions are described, it is to be understood that aspects of the invention are not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

As used herein, the term "mitochondrial transport protein" refers to any protein that is involved in the transport of mitochondria in a cell, e.g., a neuron. Mitochondrial transport factors include, but are not limited to, Mitochondrial Rho (Miro) proteins, trafficking kinesin (TRAK) proteins, kinesin, dynein motors, and myosin motors.

As used herein, the terms "Mitochondrial Rho", "Miro" and "Miro protein" all refer to a member of the mitochondrial Rho protein family of Rho GTPases. Miro family members have tandem GTP-binding domains, two EF hand domains that bind calcium and are larger than classical small GTPases. Examples of Miro family members include, but are not limited to, Miro1 (also known as "Arht1" and "mitochondrial Rho GTPase 1", "mitochondrial Rho 1", "ras homolog family member T1", and "Rhot1", the sequence for which can found at GenBank Accession Numbers NP_001028738.1 and NM_001033566.1) and Miro2 (also known as "Arht2", "mitochondrial Rho GTPase 2", "mitochondrial Rho 2" and "ras homolog family member T2", and "Rhot2", GenBank Accession Numbers NP_00620124.1 and NM_138769.2).

As used herein, the terms "trafficking kinesin protein", "TRAK" and "TRAK protein" refer to any family member of the trafficking kinesin/Milton family of kinesin adaptors. TRAK proteins (also known as Milton proteins) contain coiled coil domains and promote mitochondrial transport by linking kinesin heavy chain (KHC) to mitochondria by their direct association with Miro 1/2. Examples of TRAK proteins include, but are not limited to, TRAK1 (also known as "trafficking protein, kinesin binding 1", "MILT1", "OIP106", the sequence for which can found at GenBank Accession Numbers NM_001042646.2 and NP_001036111.1) and TRAK2 (also known as "trafficking protein, kinesin binding 2", "LS2CR3", "CALS-C", "GRIF-1", "GRIF1", "MILT2" and "OIP98", the sequence for which can be found at NM_015049.2 and NP_0055864.2).

As used herein, the term kinesin heavy chain (Khc) refers to the motor subunit of kinesin (e.g., kinesin 1, 2, 3, 4, 13, and 14) that forms a protein dimer that binds two kinesin light chains and helps to promote anterograde intracellular transport. Khcs can include a globular head (the motor domain) at the amino terminal end connected via a short flexible neck linker to long, central alpha-helical coiled-coil stalk that ends in a carboxy terminal tail domain that associates with kinesin light chains. Khcs include, but are not limited to, KIF5A (also known as "D12S1889", "MY050", "NKHC" and "SPG10", the sequences for which can found at GenBank Accession Numbers NM_004984.2 and NP_004975.2), KIF5B (also known as "KINH", "KNS", "KNS1" and "UKHC", the sequences for which can found at GenBank Accession Numbers NM_004521.2 and NP_004512.1), KIF5C (also known as "KINN", "NKHC", "NKUC-2" and "NKHC2", the sequences for which can found at GenBank Accession Numbers NM_004522.2 and NP_004513.1) and K1F2A (also known as "HK2" and "KIF2", the sequences for which can found at GenBank Accession Numbers NM_001098511.2 and NP_001091981.1).

As used herein, the term "mitochondrial disease" refers to any disease or disorder caused by dysfunctional mitochondria including, but not limited to, diseases that are related to dysfunction in mitochondrial biogenesis and homeostasis. Examples of mitochondrial diseases include, but are not limited to, mitochondrial myopathies, e.g., chronic progressive external ophthalmoplegia (CPEO), Kearns Sayre syndrome (KSS), or Myoclonus epilepsy ragged-red fibers (MERRF); Leigh's syndrome (subacute sclerosing encephalopathy); Myoneurogenic gastrointestinal encephalopathy (MNGIE); Diabetes mellitus and deafness (DAD); mitochondrial encephalomyopathy, lactic acidosis and stroke-like episodes (MELAS); or a mitochondrial neuropathy, e.g., Parkinson's Disease (PD), Neuropathy ataxia retinitis pigmentosa (NARP), or Leber's hereditary optic neuropathy (LHON).

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

Compositions and Methods for Treatment of Mitochondrial Diseases

Provided herein are compositions and methods for the treatment of mitochondrial diseases. By a "mitochondrial disease", it is meant a disease or disorder caused by dysfunctional mitochondria. By mitochondria it is meant the organelles that generate energy for the cell by converting the energy of food molecules into the ATP that powers most cell functions. Mitochondrial diseases are often caused by mutations in mitochondrial or nuclear DNA that encode proteins that affect mitochondrial biogenesis and function. The subclass of these diseases that have neuromuscular disease symptoms are often referred to as mitochondrial myopathies. Examples of mitochondrial diseases include, but are not limited to, mitochondrial myopathies, e.g., chronic progressive external ophthalmoplegia (CPEO), Kearns Sayre syndrome (KSS), or Myoclonus epilepsy ragged-red fibers (MERRF); Leigh's syndrome (subacute sclerosing encephalopathy); Myoneurogenic gastrointestinal encephalopathy (MNGIE); Diabetes mellitus and deafness (DAD); mitochondrial encephalomyopathy, lactic acidosis and stroke-like episodes (MELAS); or a mitochondrial neuropathy, e.g., Parkinson's Disease (PD), Neuropathy ataxia retinitis pigmentosa (NARP), or Leber's hereditary optic neuropathy (LHON). In further describing aspects of the invention, the following description focuses on the mitochondrial neuropathy Parkinson's Disease. However, the subject methods and the reagents, devices and kits thereof also find use in the treatment of other mitochondrial diseases as well, as described herein and as known in the art.

Inhibitors of Mitochondrial Transport Proteins

Provided herein are inhibitors of mitochondrial transport proteins (e.g. a Miro protein, a TRAK protein, or Khc). As used herein, an "inhibitor" refers to an agent that antagonizes, inhibits, suppresses or negatively regulates the activity of a protein, in this instance, a mitochondrial transport protein. As discussed above, mitochondrial transport proteins are proteins that are involved in the transport of mitochondria in a cell, e.g., transport of mitochondria from a neuron cell body to and along an axon. Mitochondrial transport factors include, but are not limited to, Mitochondrial Rho (Miro) proteins, trafficking kinesin (TRAK) proteins, and kinesin heavy chain (Khc). In some embodiments, the inhibitor is a Miro inhibitor. In certain embodiments, the inhibitor is a Miro1 inhibitor. In certain other embodiments, the inhibitor is a Miro2 inhibitor. In some embodiments, the inhibitor is a TRAK protein inhibitor. In certain embodiments, the inhibitor is a TRAK1 inhibitor. In certain other embodiments, the inhibitor is a TRAK2 inhibitor. In some embodiments, the inhibitor is a kinesin heavy chain inhibitor.

Inhibitors of mitochondrial transport proteins (referred to interchangeably herein as the "subject inhibitor" or "subject inhibitors") may inhibit the activity of their target protein by a variety of different mechanisms. For example, in some embodiments, the inhibitor reduces expression of the mitochondrial transport protein gene, e.g. reducing the production of RNA and/or protein. In other embodiments, the inhibitor reduces the function of the target protein, e.g. by binding to target protein and interfering with the ability of the target protein to bind or act (e.g., transport of mitochondria in a cell, for example, transport of mitochondria from a neuron cell body to axons.). In other embodiments, the inhibitor modulates the function of a protein upstream of the target protein, e.g. inhibiting a protein that activates the target protein, or activating a protein that inhibits the target protein.

Inhibitors of mitochondrial transport proteins will typically inhibit the level or biological activity of mitochondrial transport proteins by 20% or more, for example, 30% or more, 40% or more, or 50% or more, sometimes 60% or more, 70% or more, or 80% or more, e.g. 90%, 95%, or 100%, relative to an untreated control not contracted with the mitochondrial transport protein inhibitor. An inhibitor of a mitochondrial transport protein may be validated as such by any convenient method in the art for detecting the level and/or activity of the target mitochondrial transport protein in the presence versus absence of the subject inhibitor.

For example, the level and/or the phosphorylation state of a Miro protein (Ser156, Thr298 or Thr299 of Miro1 and Miro2, see, e.g., Wang et al. Cell 2011, 147(4): 893-906) or of Khc (Ser residues, see, e.g., Lee and Hollenbeck J Biol Chem. 1995 270(10):5600-5) may be detected, for example by immunoprecipitation with a mitochondrial transport protein-specific antibody followed by Western blotting with a phospho-specific antibody, where an increase in phosphorylation of Miro proteins or a decrease in phosphorylation of Khc following contact with the agent may indicate that the agent will treat mitochondrial disease. As another example, the level and/or the ubiquitination of a Miro protein, of a TRAK protein, or of Khc may be detected, for example by immunoprecipitation with a mitochondrial transport protein-specific antibody followed by Western blotting with a ubiquitin-specific antibody, where an increase in ubiquitination following contact with the candidate agent indicates that the agent will treat mitochondrial disease. As another example, the ability of the target mitochondrial protein to transport mitochondria within a cell may be assessed by, for example, treating cultured cells (e.g., neurons) with the subject inhibitor and observing the transport of mitochondria in the cells as compared to cells not treating with the subject inhibitor, e.g., using live cell imaging techniques (see, e.g., Brickley and Stephenson J. Biol Chem 286(20): 18079-92 (2011); Misko et al. J Neurosci 30(19): 4232-40 (2010); Russo G J et al. J. Neurosci 29(17):5443-55 (2009)). As another example, because the formation of a complex between Miro (e.g., Miro 1 and 2), TRAK (e.g., TRAK1 and 2), and Khc is essential for mitochondrial transport in neurons (see e.g., Brickley and Stephenson J. Biol Chem 286(20): 18079-92 (2011)), the effect of an inhibitory agent on Miro, TRAK, or Khc function may be assessed by assessing the ability of Miro, TRAK and Khc to form a complex in the presence of the subject inhibitor. Such an assessment can be performed using any technique to determine protein-protein interaction including, but not limited to, co-immunoprecipitation and affinity purification techniques. As another example, the ability of an agent to inhibit a mitochondrial transport protein may be assessed by assessing mitochondrial length in cells treated with agent. As discussed in the examples below, inhibitors of mitochondrial transport proteins can decrease mitochondrial length in particular cells (e.g., motor neurons). In certain embodiments, the ability of the inhibitor of a mitochondrial transport protein to decrease mitochondrial length is assessed in a motor neuron. In specific embodiments, the ability is assessed in a cell having a familial PD mutation, e.g. a PINK1 or LRRK2 mutation.

For example, in certain embodiments, the subject inhibitor is a nucleic acid inhibitor (e.g., antisense inhibitor, shRNA agent, siRNA agent, etc.) that acts on the target gene or mRNA to inhibit the amount of the target mitochondrial transport protein produced, thereby reducing the amount of mitochondrial transport protein activity in the targeted cells, where the target cell may be present in vitro or in vivo. By "reducing the amount of" is meant that the level or quantity of the target mitochondrial transport protein in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods. Changes in amounts of target protein may be readily detected by a number of methods known in the art, e.g., Western blotting, ELISA, etc.

For example, in certain embodiments, the subject inhibitor is an antisense agent. An antisense agent may be antisense oligonucleotides (ODN), particularly synthetic ODN having chemical modifications from native nucleic acids, or nucleic acid constructs that express such antisense molecules as RNA. The antisense sequence is complementary to the targeted mRNA, and inhibits its translation into protein. One or a combination of antisense molecules may be administered, where a combination may comprise multiple different sequences.

Antisense molecules may be produced by expression of all or a part of the target mitochondrial transport protein analog sequence in an appropriate vector, where the transcriptional initiation is oriented such that an antisense strand is produced as an RNA molecule. Alternatively, the antisense molecule may be a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like. In certain embodiments the inhibitor of the mitochondrial transport protein is an antisense oligonucleotide that is 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides in length. In certain embodiments the inhibitor of SF2 is an antisense oligonucleotide that is 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides in length.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of modifications that alter the chemistry of the backbone, sugars or heterocyclic bases have been described in the literature, any of which may be included in the antisense agent. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Antisense agents of interest also include antagomir RNAs, e.g., as described by Krutzfeldt et al., supra, herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing mRNAs in vivo, chemically modified, cholesterol-conjugated single-stranded RNA analogues complementary to mRNAs were developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

In certain embodiments, the subject inhibitor is an RNAi agent. By RNAi agent is meant an agent that modulates expression of a gene by an RNA interference mechanism.

The RNAi agents employed in one embodiment are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. In certain embodiments, the oligoribonucleotide is less than 100, 95, 90, 85, 80, 75, 70, 65, 60, 55, 50, 45 or 40 nt in length. In certain embodiments, the oligoribonucleotide is less than 100 nt in length. In other embodiments, the oligoribonucleotide is less than 95 nt in length. In another embodiment, the oligoribonucleotide is less than 90 nt in length. In another embodiment, the oligoribonucleotide is less than 85 nt in length. In some embodiments, the oligoribonucleotide is less than 80 nt in length. In other embodiments, the oligoribonucleotide is less than 75 nt in length. In other embodiments, the oligoribonucleotide is less than 70 nt in length. In other embodiments, the oligoribonucleotide is less than 65 nt in length. In yet other embodiments, the oligoribonucleotide is less than 60 nt in length. In other embodiments, the oligoribonucleotide is less than 55 nt in length. In certain embodiments, the oligoribonucleotide is less than 50 nt in length. In other embodiments, the oligoribonucleotide is less than 45 nt in length. In yet other embodiments, the oligoribonucleotide is less than 40 nt in length. In specific embodiments, the oligoribonucleotide is 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41 or 40 nt in length.

Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. In certain embodiments, the RNA agent is 30, 29, 28, 27, 26, 25, 24, 23, 22, 21, 20, 19, 18, 17, 16, 15, 14, 13, 12, 11 or 10 bp in length. In such embodiments, the inhibitor of the mitochondrial transport protein may be said to be a target-specific siRNA, e.g. a mitochondrial transport protein siRNA.

Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons. In such embodiments, the inhibitor of the mitochondrial transport protein may be said to be a target-specific shRNA, e.g. a Miro protein specific shRNA, a TRAK protein specific shRNA, or a Khc specific shRNA.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, (e.g., an siRNA or shRNA) as described above, the RNAi agent may encode an interfering ribonucleic acid as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

In another embodiment, the subject inhibitor is an antibody that is specific for the mitochondrial transport protein (e.g. a Miro, TRAK or Khc specific antibody). The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity. Antibodies that can be used as mitochondrial transport protein inhibitor may be obtained from a suitable commercial source (e.g., anti-Miro1 antibody (Catalog Number ab55035; AbCam; Cambridge, Mass.), anti-Miro2 antibody (Catalog Number ab67588; AbCam; Cambridge, Mass.), anti-TRAK1 antibody (Catalog Number ab28751; AbCam; Cambridge, Mass.), anti-TRAK2 antibody (Catalog Number ab110947; AbCam; Cambridge, Mass.), and anti-Khc antibody Catalog Number ab9097; AbCam; Cambridge, Mass.).

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a Class II target antigen comprising an antigenic portion of the polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Freund's, Freund's complete, oil-in-water emulsions, etc.) Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones, which co-express a heavy and light chain (resembling the Fab fragment or antigen binding fragment of an antibody molecule). The vectors that carry these genes are co-transfected into a host (e.g., bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Antibodies with a reduced propensity to induce a violent or detrimental immune response in humans (such as anaphylactic shock), and which also exhibit a reduced propensity for priming an immune response which would prevent repeated dosage with the antibody therapeutic are preferred for use in the invention. Thus, humanized, single chain, chimeric, or human antibodies, which produce less of an immune response when administered to humans, are preferred for use in the present invention. Also included in the invention are multi-domain antibodies.

A chimeric antibody is a molecule in which different portions are derived from different animal species, for example those having a variable region derived from a murine mAb and a human immunoglobulin constant region. Techniques for the development of chimeric antibodies are described in the literature. See, e.g., Morrison et al. (1984) *Proc. Natl. Acad. Sci.* 81:6851-6855; Neuberger et al. (1984) *Nature* 312:604-608; Takeda et al. (1985) *Nature* 314:452-454. Single chain antibodies are formed by linking the heavy and light chain fragments of the Fv region via an amino acid bridge, resulting in a single chain polypeptide. See, e.g., Huston et al., *Science* 242:423-426; *Proc. Natl. Acad. Sci.* 85:5879-5883; and Ward et al. *Nature* 341:544-546.

In addition to entire immunoglobulins (or their recombinant counterparts), immunoglobulin fragments comprising the epitope binding site (e.g., Fab', F(ab')$_2$, or other fragments) are useful as antibody moieties in the methods described herein. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Antibody fragments that recognize specific epitopes may be generated by techniques well known in the field. For instance, F(ab')$_2$ fragments can be produced by pepsin digestion of the antibody molecule, and Fab fragments can be generated by reducing the disulfide bridges of the F(ab')$_2$ fragments. Single chain antibodies (Fv) can be produced from phage libraries containing human variable regions. See U.S. Pat. No. 6,174,708. Intrathecal administration of single-chain immunotoxin, LMB-7 [B3(Fv)-PE38], has been shown to cure of carcinomatous meningitis in a rat model. *Proc Natl. Acad. Sci USA* 92, 2765-9, all of which are incorporated by reference fully herein.

In certain embodiments, the subject inhibitor is a F(ab')$_2$ fragment. In other embodiments, the subject inhibitor is an Fab' fragment. In other embodiments, the subject inhibitor is an Fv immunoglobulin. Antibody inhibitors, in particular, can be tested by any suitable standard means, e.g., ELISA assays, etc. As a first test, the antibodies may be tested for binding against the immunogen. After selective binding is established, the candidate antibody may be tested for appropriate activity in an in vivo model.

In some embodiments, the subject inhibitor is a small molecule (i.e. "a small molecule inhibitor"). By a "small molecule" it is meant a naturally occurring or synthetic small molecule compound, including numerous chemical classes, though typically they are organic molecules, e.g. small organic compounds having a molecular weight of more than 50 and less than about 2,500 daltons. Small molecule inhibitors of mitochondrial transport proteins may comprise functional groups necessary for structural interactions, particularly hydrogen bonding, and typically include at least an amine, carbonyl, hydroxyl or carboxyl group, frequently at least two of the functional chemical groups. These small molecule inhibitors often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Compounds may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In certain embodiments, the subject small molecule inhibitor is an organic molecule comprising functional groups necessary for structural interactions, particularly hydrogen bonding, and typically include at least an amine, carbonyl, hydroxyl or carboxyl group, frequently at least two of the functional chemical groups. The subject inhibitor may comprise cyclical carbon or heterocyclic structures and/or aromatic or polyaromatic structures substituted with one or more of the above functional groups. Subject inhibitors are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition.

An agent may be tested to confirm its biological activity as an inhibitor of mitochondrial transport protein (e.g., Miro, TRAK protein, or Khc) activity by adding the agent to one or a plurality of cell samples (e.g., neurons), usually in conjunction with cells lacking the agent. The change in parameters in response to the agent is measured, and the result evaluated by comparison to reference cultures, e.g., in the presence and absence of the agent, obtained with other agents, etc. Non-limiting examples of parameters that may be measured include the phosphorylation state of the mitochondrial transport protein; the ability of mitochondrial transport proteins to form complexes for mitochondrial transport and the ability of a cell sample (e.g. neuronal cell sample) to transport mitochondria.

Antibody and small molecule inhibitors may be screened using a variety of methods to detect target binding in vitro and in vivo. e.g., ELISA assays, etc. These methods include, but are not limited to, methods that measure binding affinity to a target, biodistribution of the compound within an animal or cell, or compound mediated cytotoxicity. As a first test, the antibody or small molecule may be tested for binding against the target mitochondrial transport protein. After selective binding is established, the candidate antibody may be tested for appropriate activity in an in vivo model. These and other screening methods known in the art provide information on the ability of a compound to bind to, modulate, or otherwise interact with the specified target and are a measure of the compound's efficacy.

The mitochondrial transport protein inhibitor described herein may be administered alone or in combination with any pharmaceutically acceptable carrier or salt known in the art and as described below.

Pharmaceutical Compositions

In some aspects of the invention, the inhibitors disclosed herein are provided in a pharmaceutical composition, wherein the pharmaceutical composition comprises a therapeutically effective amount of one or more of the mitochondrial transport proteins (e.g., Miro, TRAK protein, or Khc) inhibitors provided herein, together with a suitable amount of carrier so as to provide the form for proper administration to a patient.

The term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" or "vehicle" refers to a diluent, adjuvant, excipient, or vehicle with which the mitochondrial transport protein inhibitor is administered. Such pharmaceutical carriers can be, for example, lipids, e.g. liposomes, e.g. liposome dendrimers; sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The inhibitors can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin, hereby incorporated by reference herein in its entirety. Such compositions will contain a therapeutically effective amount of the mitochondrial transport protein (e.g. a Miro protein, a TRAK protein, or Khc) inhibitor, preferably in purified form, together with a suitable amount of carrier so as to provide the form for proper administration to the patient. The formulation should suit the mode of administration.

The pharmaceutical composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process.

The subject pharmaceutical composition is typically sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The pharmaceutical composition may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The pharmaceutical composition comprising the lyophilized inhibitor(s) is prepared by reconstituting the lyophilized compound, for example, by using bacteriostatic Water-for-Injection.

The pharmaceutical composition can be formulated for intravenous, oral, via implant, transmucosal, transdermal, intramuscular, intrathecal, or subcutaneous administration. In some embodiments, the pharmaceutical composition is formulated for intravenous administration. In other embodiments, the pharmaceutical composition is formulated for subcutaneous administration. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGAs). Implantable systems include rods and discs, and can contain excipients such as PLGA and polycaprylactone. Osteopontin or nucleic acids of the invention can also be administered attached to particles using a gene gun.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

In certain embodiments, the subject pharmaceutical composition is formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. A BBB disrupting agent can be co-administered with the therapeutic compositions when the compositions are administered by intravascular injection. Other strategies to go through the BBB may entail the use of endogenous transport systems, including caveoil-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of the ND pharmaceutical composition behind the BBB may be by local delivery, for example by intrathecal delivery, e.g., through an Ommaya reservoir (see, e.g., U.S. Pat. Nos. 5,222,982 and 5,385,582, incorporated herein by reference); by bolus injection, e.g., by a syringe, e.g., intravitreally or intracranially; by continuous infusion, e.g., by cannulation, e.g., with convection (see, e.g., US Application No. 20070254842, incorporated here by reference); or by implanting a device upon which the inhibitor pharmaceutical composition has been reversably affixed (see e.g., US Application Nos. 20080081064 and 20090196903, incorporated herein by reference).

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, the pharmaceutical composition is supplied as a water free concentrate. In some embodiments, the pharmaceutical composition is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Methods of Treatment

In some aspects of the invention, methods are provided for the treatment or amelioration of a mitochondrial disease, e.g. a mitochondrial myopathy, e.g. chronic progressive external ophthalmoplegia (CPEO), Kearns Sayre syndrome (KSS), or Myoclonus epilepsy ragged-red fibers (MERRF); Leigh's syndrome (subacute sclerosing encephalopathy); Myoneurogenic gastrointestinal encephalopathy (MNGIE); Diabetes mellitus and deafness (DAD); mitochondrial encephalomyopathy, lactic acidosis and stroke-like episodes (MELAS); or a mitochondrial neuropathy, e.g., Parkinson's Disease (PD), Neuropathy ataxia retinitis pigmentosa (NARP), or Leber's hereditary optic neuropathy (LHON), and the like, in a subject having or at risk for developing the mitochondrial disease, the method comprising administering to the subject a therapeutically effective amount of the subject inhibitor(s), i.e. mitochondrial transport protein (e.g. a Miro protein, a TRAK protein, or Khc) inhibitor(s) or pharmaceutical composition thereof as described herein. In other words, cells of the subject, e.g. neuron or muscle cells, are contacted in vivo with one or more of the subject inhibitors. For example, in the treatment of a subject having Parkinson's Disease, one or more neurons, e.g. dopaminergic neurons, e.g. a dopaminergic neuron residing in the substantia nigra of the midbrain and/or putamen, is contacted with one or more of the subject inhibitor(s). Cells in vivo may be contacted with one or more of the subject inhibitors suitable for pharmaceutical use by any convenient method for the administration of polypeptides, and nucleic acids, or small molecules to a subject, e.g. as described herein or known in the art. Often, the subject is a mammal. Mammalian species that may be treated with the present methods include canines; felines; equines; bovines; ovines; etc. and primates, particularly humans. In some embodiments, the method is for the treatment of a human. Animal models, particularly small mammals, e.g., murine, lagomorpha, etc. may be used for experimental investigations.

By a "therapeutically effective amount" of the subject inhibitor it is meant an amount that is required to reduce the severity, the duration and/or the symptoms of the mitochondrial disease, e.g. as described herein or as known in the art. For example, the therapeutically effective amount may slow the rate of progression of the disease and the increase of severity of clinical symptoms, may halt the progression of the disease and the clinical symptoms, or may cause a regression of the disease and the clinical symptoms. In some instances, the method further comprises the step of measuring one or more of the clinical symptoms of the mitochondrial disease, e.g. motor symptoms, neuronal symptoms, etc., e.g. as described herein or known in the art before and/or after treatment with the subject inhibitor(s) and determining that the one or more symptoms have been reduced.

The calculation of the effective amount or effective dose of the inhibitor or pharmaceutical composition to be administered is within the skill of one of ordinary skill in the art, and will be routine to those persons skilled in the art by using assays known in the art, e.g. as described herein. The effective amount of an inhibitor or pharmaceutical composition to be given to a particular patient will depend on a variety of factors, several of which will differ from patient to patient. A competent clinician will be able to determine an effective amount of a therapeutic agent to administer to a patient to halt or reverse the progression the disease condition as required. For example, the effective amount may be dependent upon the route of administration and the seriousness of the mitochondrial disease, and should be decided according to the judgment of the practitioner and each human patient's circumstances.

Determining a therapeutically effective amount of the inhibitor can be done based on animal data using routine computational methods. For example, effective amounts may be extrapolated from dose-response curves derived from preclinical protocols either in vitro (e.g., dopaminergic neuron cultures, such as the ones described below, treated with rotenone or MPP+ for 24 h, or with Epoxymicin for 48 h) or using any of the in vivo mitochondrial disease animal models known in the art (e.g., 6-hydroxydopamine (6-OHDA) rat model, MPTP mouse or primate model or rotenone model). See, for example, Duty et al., *Br J Pharmacol.* 164(4): 1357-1391 (2011), incorporated herein by reference. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

In some embodiments, the effective amount of the pharmaceutical composition provided herein is between about 0.025 mg/kg and about 1000 mg/kg body weight of a human subject. In certain embodiments, the pharmaceutical composition is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of the pharmaceutical composition provided herein is between about 0.025 mg/kg and about 60 mg/kg body weight of a human subject. In some embodiments, the effective amount of an antibody of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

The subject inhibitor(s) can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized. The inhibitor be administered daily, semi-weekly, weekly, semi-monthly, monthly, etc., at a dose of from about 0.01 mg, from about 0.1 mg, from about 1 mg, from about 5 mg, from about 10 mg, from about 100 mg or more per kilogram of body weight when administered systemically. Smaller doses may be utilized in localized administration, e.g., in direct administration to ocular nerves, etc.

Administration of the subject inhibitor(s) can be achieved in various ways, including oral, buccal, rectal, parenteral, intraperitoneal, intradermal, transdermal, intracheal, intracranial, intraventricular, intracerebral, etc., administration. The pharmaceutical composition comprising the inhibitor may be systemic after administration or may be localized by the use of regional administration, intramural administration, or use of an implant that acts to retain the active dose at the site of implantation. As discussed above, the pharmaceutical composition comprising the subject inhibitor(s) may be formulated for immediate activity or they may be formulated for sustained release.

In certain embodiments, the subject mitochondrial transport protein (e.g. a Miro protein, a TRAK protein, or Khc) inhibitor or pharmaceutical composition thereof is administered in combination with a second therapeutic agent for the treatment or amelioration of the mitochondrial disease. For example, if the mitochondrial disease is Parkinson's disease, the subject methods may comprise administration of a second therapeutic agent known in the art to treat Parkinson's disease, e.g., levodopa (alone or in combination with a dopa decarboxylase inhibitor or COMT inhibitor), dopamine agonists (e.g., bromocriptine, pergolide, pram ipexole, ropinirole, piribedil, cabergoline, apomorphine, and lisuride), MAO-B inhibitors (e.g., selegiline and rasagiline), amantadine, an anticholinergic, or a polypeptide, peptide, antibody, nucleic acid, or small molecule that acts as a PUM1 antagonist, an SR protein antagonist, a Parkin agonist, a PINK1 agonist, an 4E-BP1 agonist, a Drp1 agonist, an Atg1 agonist, a TauS2A agonist, a Rbf1 agonist, a Dp antagonist, an E2f1 antagonist, a Polo-like kinase 2 antagonist or a Notch agonist. By an agonist, it is meant an agent that induces, promotes, enhances the expression or activity of a gene or gene product, for example, a cDNA that encodes one of the aforementioned gene products, a polypeptide or peptide mimetic that encodes one of the aforementioned gene products, a polypeptide or peptide that encodes a protein that activates one of the aforementioned gene products, an activating antibody that is specific for one of the aforementioned gene products, and the like. By an antagonist, it is meant an agent that reduces, suppresses, or inhibits the expression or activity of a gene or gene product, for example, an RNA (e.g. siRNA, antisense RNA, etc., as described elsewhere herein or known in the art) that is specific for one of the aforementioned gene products, a blocking antibody that is specific for one of the aforementioned gene products, or a small molecule that inhibits the activity of one of the aforementioned gene products). In some embodiments, the subject inhibitor(s) are provided at the same time as the additional therapeutic. In some embodiments, the subject inhibitor(s) are provided before the additional therapeutic. In some embodiments, the subject inhibitor(s) are provide after the additional therapeutic.

Utility

The subject compositions and methods find use in the treatment of mitochondrial diseases. By a mitochondrial disease, it is meant any disease associated with mitochondrial function, for example, a mitochondrial myopathy, e.g., chronic progressive external ophthalmoplegia (CPEO), Kearns Sayre syndrome (KSS), or Myoclonus epilepsy ragged-red fibers (MERRF); Leigh's syndrome (subacute sclerosing encephalopathy); Myoneurogenic gastrointestinal encephalopathy (MNGIE); Diabetes mellitus and deafness (DAD); mitochondrial encephalomyopathy, lactic acidosis and stroke-like episodes (MELAS); or a mitochondrial neuropathy, e.g., Parkinson's Disease (PD), Neuropathy ataxia retinitis pigmentosa (NARP), Leber's hereditary optic neuropathy (LHON); and the like.

Chronic Progressive External Ophthalmoplegia.

Chronic progressive external ophthalmoplegia (abbreviated CPEO) is a mitochondrial myopathy syndrome that is characterized by isolated involvement of the muscles controlling eyelid movement (levator palpebrae, orbicularis oculi), and those controlling eye movement (extra-ocular muscles). This results in ptosis and ophthalmoplegia respectively. CPEO is most commonly caused by the mitochondrial DNA point mutation A3243G.

Kearns-Sayre Syndrome.

Kearns-Sayre syndrome (KSS) also known as oculocraniosomatic disease or Oculocraniosomatic neuromuscular disease with ragged red fibers, is a slowly progressive multisystem mitochondrial disease with a typical onset before 20 years of age. KSS is a more severe syndromic variant of CPEO. KSS involves a paralysis of the same eye muscles as in CPEO. In addition, bilateral pigmentary retinopathy and cardiac conduction abnormalities are observed. Other areas of involvement can include cerebellar ataxia, proximal muscle weakness, deafness, diabetes mellitus, growth hormone deficiency, hypoparathyroidism, or other endocrinopathies. As with CPEO, muscle involvement may begin unilateral but always develops into a bilateral deficit, and the course is progressive. KSS is usually caused by a single large deletion of genetic material within the mitochondrial DNA. These deletions, over 150 of which have been observed, are typically spontaneous. Less frequently, the mutation is transmitted by the mother.

Myoclonus Epilepsy Ragged-Red Fibers.

Myoclonus epilepsy ragged-red fibers (MERRF) syndrome is a progressive multi-system syndrome usually beginning in childhood, but onset may occur in adulthood. The rate of progression varies widely. Onset and extent of symptoms can differ among affected siblings. Symptoms include progressive myoclonic epilepsy, "Ragged Red Fibers", in which clumps of diseased mitochondria accumulate in the subsarcolemmal region of the muscle fiber and appear as ragged red fibers" when muscle is stained with modified Gömöri trichrome stain, short stature, hearing loss, lactic acidosis, exercise intolerance, and poor night vision. Other symptoms may include epileptic seizures, and ataxia.

Over 80% of MERRF cases are caused by a maternally-inherited mutation at position 8344 in the mitochondrial genome. This point mutation disrupts the mitochondrial gene encoding the transfer RNA tRNA-Lysine (MT-TK gene in humans). Other mutations associated with MERRF include mutations on the genes MT-TL1 (encoding the tRNA leucine 1), MT-TH (encoding tRNA histidine), MT-TS1 (encoding serine 1), MT-TS2 (encoding serine 2), and MT-TF (encoding tRNA phenylalanine).

Leigh Syndrome.

Leigh syndrome, also known as juvenile subacute necrotizing encephalomyelopathy, Leigh syndrome, infantile subacute necrotizing encephalomyelopathy, and subacute necrotizing encephalomyelopathy (SNEM), is a rare neurometabolic disorder that affects the central nervous system. The symptoms of Leigh's disease typically begin within a year of a child's birth and lead to death within a span of several years, though symptoms can appear anytime between the ages of three months and two years or very rarely in adolescence or adulthood. Infants with the syndrome have symptoms that include diarrhea, vomiting, and dysphagia (trouble swallowing or sucking), leading to a failure to thrive. Children with early Leigh disease also may appear irritable and cry much more than usual. Seizures are often seen. Excess lactate may be seen in the urine, cerebrospinal fluid, and blood of a person with Leigh syndrome in a condition called lactic acidosis. As the disease progresses, the muscular system is debilitated throughout the body, as the brain cannot control the contraction of muscles. Hypotonia (low muscle tone and strength), dystonia (involuntary, sustained muscle contraction), and ataxia (lack of control over movement) are often seen in people with Leigh's disease. The eyes are particularly affected; the muscles that control the eyes become weak, paralyzed, or uncontrollable in conditions called ophthalmoparesis (weakness or paralysis) and nystagmus (involuntary eye movements). The heart and lungs can also fail as a result of Leigh's disease. Hypertrophic cardiomyopathy, thickening of part of the heart muscle, is also sometimes found and can cause death. However, respiratory failure is the most common ultimate cause of death in people with Leigh syndrome. Other neurological symptoms include peripheral neuropathy, loss of sensation in extremities caused by damage to the peripheral nervous system.

At least 26 genetic mutations have been identified that cause Leigh syndrome. These include mutations that result in a pyruvate dehydrogenase (PDHC) deficiency, and mutations in respiratory chain enzymes, Complexes I, II, IV, and V. Both familial (i.e. inherited) and sporadic forms of the disease exist.

Myoneurogenic Gastrointestinal Encephalopathy.

Myoneurogenic gastrointestinal encephalopathy (MNGIE) is a multisystem disorder that usually appears between the second and fifth decades of life. Abnormalities of the digestive system are among the most common and severe features of MNGIE disease. Gastrointestinal symptoms may include gastrointestinal dysmotility possibly resulting in pseudo-obstruction in which the muscular contractions (peristalsis) of the gastrointestinal tract become inefficient causing malabsorption. Borborygmi (stomach rumbling), early satiety, diarrhea, constipation, gastroparesis, nausea, vomiting, weight loss, and diverticulitis can occur.

MNGIE is also characterized by abnormalities of the nervous system, although these tend to be milder than the gastrointestinal problems. Affected individuals experience tingling, numbness, and weakness in their limbs (peripheral neuropathy), particularly in the hands and feet. Additional neurological signs and symptoms can include droopy eyelids (ptosis), weakness of the muscles that control eye movement (ophthalmoplegia), and hearing loss. Leukoencephalopathy, which is the deterioration of the white matter of the brain, is a hallmark. These changes in the brain can be seen with magnetic resonance imaging (MRI).

Diabetes Mellitus and Deafness.

Diabetes mellitus and deafness (DAD), and more particularly, maternally inherited diabetes and deafness (MIDD), is a form of diabetes that is often accompanied by hearing loss, especially of high tones. The diabetes in MIDD is characterized by hyperglycemia resulting from a shortage of the hormone insulin. In MIDD, the diabetes and hearing loss usually develop in mid-adulthood, although the age that they occur varies from childhood to late adulthood. Typically, hearing loss occurs before diabetes.

In some instances, MIDD may be associated with the eye disorder called macular retinal dystrophy, which is characterized by colored patches in the light-sensitive tissue that lines the back of the eye (the retina). This disorder does not usually cause vision problems in people with MIDD. Individuals with MIDD also may experience muscle cramps or weakness, particularly during exercise; heart problems; kidney disease; and constipation. Individuals with MIDD are often shorter than their peers.

MIDD is most commonly caused by mutations in the mitochondrial genes MT-TL1, MT-TK, or MT-TE genes (encoding tRNA leucine 1, tRNA lysine, and tRNA glutamic acid, respectively).

Mitochondrial Encephalomyopathy, Lactic Acidosis, and Stroke-Like Episodes.

Mitochondrial encephalomyopathy, lactic acidosis, and stroke-like episodes (MELAS) is a multisystem condition that affects the brain and nervous system (encephalo-) and muscles (myopathy). The signs and symptoms of this disorder most often appear in childhood following a period of normal development, although they can begin at any age. Early symptoms may include muscle weakness and pain, recurrent headaches, loss of appetite, vomiting, and seizures. Stroke-like episodes, often accompanied by seizures, are the hallmark symptom of MELAS and cause partial paralysis, loss of vision, and focal neurological defects. The gradual cumulative effects of these episodes often result in variable combinations of loss of motor skills (speech, movement, and eating), impaired sensation (vision loss and loss of body sensations), and mental impairment (dementia). MELAS patients may also suffer additional symptoms including: muscle weakness, peripheral nerve dysfunction, diabetes, hearing loss, cardiac and kidney problems, and digestive abnormalities. Lactic acid usually accumulates at high levels in the blood, cerebrospinal fluid, or both.

MELAS is maternally inherited due to a mutation in mitochondrial DNA. There are at least 17 different mutations that can cause MELAS, the most prevalent being the A3243G mutation, which is responsible for about 80% of the cases.

Parkinson's Disease.

Parkinson's disease (PD) also known as idiopathic or primary parkinsonism, hypokinetic rigid syndrome/HRS, or paralysis agitans, is a degenerative disorder of the central nervous system. The motor symptoms of Parkinson's disease result from the death of dopamine-generating neurons in the substantia nigra, a region of the midbrain, and putamen; the cause of this cell death is unknown. Early in the course of the disease, the most obvious symptoms are movement-related; these include shaking, rigidity, resting tremors, bradykinesia, postural stability, slowness of movement and difficulty with walking and gait. Later, thinking and behavioral problems may arise, with dementia, e.g. cognitive impairment, hallucinations, delusion, behavioral abnormalities, depression, disturbance of sleep and wakefulness, commonly occurring in the advanced stages of the disease, whereas depression is the most common psychiatric symptom. Other symptoms include sensory (loss of smell), sleep (disturbance of sleep and wakefulness) and emotional problems, constipation, hypotension, urinary frequency, impotence and sweating. Parkinson's disease is more common in older people, with most cases occurring after the age of 50.

Parkinson's Disease may be of the familial form or the sporadic form. By a familial form, it is meant that the disease is inherited, i.e. by the passage of a heritable gene mutation from parent to child through the gametes. A number of different heritable mutations have been associated with PD, including for example, mutations in PTEN-induced putative kinase 1 (PINK-1); Parkin (also known as RBR E3 ubiquitin protein ligase, or PARK2); leucine-rich repeat kinase 2 (LRRK2); alpha-Synuclein (SNCA, PARK4); ubiquitin carboxy-terminal hydrolase L1 (UCHL1); parkinson protein 7 (PARK7, DJ-1); ATPase type 13A2 (ATP13A2); phospholipase A2, group VI (PLA2G6); DnaJ (Hsp40) homolog, subfamily C, member 6 (DNAJC6, PARK19); eukaryotic translation initiation factor 4 gamma, 1 (EIF4G1, PARK18); F-box protein 7 (FBXO7); GRB10 interacting GYF protein 2 (GI-GYF2); HtrA serine peptidase 2 (HTRA2); synaptojanin 1 (SYNJ1); or vacuolar protein sorting 35 homolog (VPS35). By a sporadic form, it is meant that the disease occurs sporadically, i.e. due to sporadic mutation of a gene, e.g. one of the aforementioned genes.

Neuropathy, Ataxia, and Retinitis Pigmentosa.

Neuropathy ataxia retinitis pigmentosa (NARP) is a condition that causes a variety of signs and symptoms chiefly affecting the nervous system. Beginning in childhood or early adulthood, most people with NARP experience numbness, tingling, or pain in the arms and legs (sensory neuropathy); muscle weakness; and problems with balance and coordination (ataxia). Many affected individuals also have vision loss caused by changes in the light-sensitive tissue that lines the back of the eye (the retina). In some cases, the vision loss results from a condition called retinitis pigmentosa. This eye disease causes the light-sensing cells of the retina gradually to deteriorate. Learning disabilities and developmental delays are often seen in children with NARP, and older individuals with this condition may experience a loss of cognitive functions (dementia). Other features of NARP include seizures, hearing loss, and cardiac conduction defects. These signs and symptoms vary among affected individuals. NARP has been associated with point mutations in the mitochondrial gene MT-ATP6, which encodes one subunit of ATP synthase (also known complex V).

Leber's Hereditary Optic Neuropathy.

Leber's hereditary optic neuropathy (LHON) is an eye disorder characterized by progressive loss of central vision due to degeneration of the optic nerves and retina. Blurring and clouding of vision are usually the first symptoms of LHON. These vision problems may begin in one eye or simultaneously in both eyes; if vision loss starts in one eye, the other eye is usually affected within several weeks or months. Over time, vision in both eyes worsens with a severe loss of visual acuity and color vision. This condition mainly affects central vision, which is needed for detailed tasks such as reading, driving, and recognizing faces. Vision loss results from the death of the optic nerve. Although central vision gradually improves in a small percentage of cases, in most cases the vision loss is profound and permanent.

Vision loss is typically the only symptom of LHON; however, some families with additional signs and symptoms have been reported. In these individuals, the condition is described as "LHON plus." In addition to vision loss, the features of LHON plus can include movement disorders, tremors, and cardiac conduction defects. Some affected individuals develop features similar to multiple sclerosis, which is a chronic disorder characterized by muscle weakness, poor coordination, numbness, and a variety of other health problems.

Mutations in the mitochondrial genes MT-ND1, MT-ND4, MT-ND4L, and MT-ND6 can cause LHON. These genes encode NADH dehydrogenases, which together form Complex I of the respiratory chain.

In some embodiments, the method comprises determining if the subject has the mitochondrial disease, and then providing one or more of the subject inhibitors to treat the disease. Any convenient method for determining if the subject has the mitochondrial disease may be used, including, for example, assessing for the aforementioned symptoms or performing genetic testing to detect a gene mutation associated with the disease, e.g. as described above or as known in the art. In some embodiments, the method comprises detecting one or more of the symptoms of the disease, administering the subject inhibitor(s), and assaying for the symptom(s) after administration, where the administration of the subject inhibitor inhibits, suppress, or moderate the symptoms of the mitochondrial disease.

Screening Methods

In some aspects of the invention, methods are provided for screening candidate agents for activity in treating a mitochondrial disease in an individual having a mitochondrial disease. To that end, it has been shown that mitochondrial transport proteins, for example, Miro proteins, trafficking kinases, and the kinesin heavy chain, promote the development or progression of mitochondrial disease or the symptoms thereof. Accordingly, screening for candidate agents that inhibit the expression or activity of mitochondrial transport proteins in cells should identify agents that will be useful in treating mitochondrial disease in patients.

For example, in screening assays for biologically active agents, cells expressing the mitochondrial transport protein of interest are contacted with a candidate agent of interest and the effect of the candidate agent on the expression or function of the mitochondrial transport protein is assessed by monitoring one or more mitochondria-associated parameters. Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may comprise contacting a cell that expresses mitochondrial transport proteins with a candidate agent; and comparing the mitochondria-associated parameter to the mitochondria-associated parameter in a cell that expresses the mitochondrial transport proteins but was not contacted with the candidate agent, wherein a difference in the parameter in the cell contacted with the candidate agent indicates that the candidate agent will treat the mitochondrial disease.

One example of a mitochondria-associated parameter that may be quantified when screening for agents that will treat mitochondrial disease would be the phosphorylation state of a Miro protein (Ser156, Thr298 or Thr299 of Miro1 and Miro2), a TRAK protein, or Khc (Ser residues, see, e.g., Lee and Hollenbeck J Biol Chem. 1995 270(10):5600-5), by for example, immunoprecipitation with mitochondrial transport protein-specific antibodies followed by Western blotting with phospho-specific antibodies where an increase in phosphorylation of Miro proteins or a decrease in phosphorylation of Khc following contact with the candidate agent indicates that the candidate agent may treat mitochondrial disease. Another example of a parameter would be the state of ubiquitination of a Miro protein, a TRAK protein, or Khc, by, for example, immunoprecipitation with mitochondrial transport protein-specific antibodies followed by Western blotting with ubiquitin-specific antibodies, where an increase in ubiquitination following contact with the candidate agent indicates that the agent will treat mitochondrial disease. Yet another example would be the rate at which mitochondria are transported around the cell, measurable by, for example live cell imaging techniques, where a decrease in the rate of transport after contacting the cell with candidate agent indicates that the agent will treat mitochondrial disease. Another example would be the length of the mitochondria in a cell, where a decrease in the length of the mitochondria after contacting the cell with candidate agent indicates that the agent will treat mitochondrial disease. Other output parameters could include those that are reflective of the ability of Miro proteins, TRAK proteins, and khc to form a complex (see e.g., Brickley and Stephenson J. Biol Chem 286(20): 18079-92 (2011)) in the presence of the subject inhibitor, which may be assessed by, for example, co-immunoprecipitation or affinity purification techniques, where a decrease in complex formation after contacting the cell with candidate agent indicates that the agent will treat mitochondrial disease. In some instances, one parameter is measured. In some instances, multiple parameters are measured.

All cells comprise mitochondria, and thus, any cell may be used in the subject screening methods. In some instances, the cell is a cell type that is typically affected by mitochondrial disease, e.g. a muscle cell or a neuron, e.g. a motor neuron. In certain instances, the cell comprises a genetic mutation, i.e. a mutation in a nuclear or mitochondrial gene, which is associated with mitochondrial disease. In some instances, the cell may be acutely cultured from an individual that has a mitochondrial disease.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, or miRNA, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the cells are contacted with vectors comprising the nucleic acid of interest such that the vectors are taken up by the cells.

Methods for contacting cells with nucleic acid vectors, such as electroporation, calcium chloride transfection, and lipofection, are well known in the art. Alternatively, the nucleic acid of interest may be provided to the subject cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the nucleic acids comprising the nucleic acid are packaged into viral capsids by a packaging cell line. Different packaging cell lines provide a different envelope protein to be incorporated into the capsid, this envelope protein determining the specificity of the viral particle for the cells. Methods of introducing viral vectors comprising the nucleic acid of interest into packaging cell lines, of collecting the viral particles that are generated by the packaging lines, and of infecting cells using the packaged viral particles are well known in the art.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc.

Candidate agents of interest for screening also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

If the candidate polypeptide agent is being assayed for its ability to act intracellularly, the polypeptide may comprise the polypeptide sequences of interest fused to a polypeptide permeant domain. A number of permeant domains are known in the art and may be used in the non-integrating polypeptides of the present invention, including peptides, peptidomimetics, and non-peptide carriers. For example, a permeant peptide may be derived from the third alpha helix of Drosophila melanogaster transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include polyarginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The polypeptide may be formulated for improved stability. For example, the peptides may be PEGylated, where the polyethyleneoxy group provides for enhanced lifetime in the blood stream. The polypeptide may be fused to another polypeptide to provide for added functionality, e.g. to increase the in vivo stability. Generally such fusion partners are a stable plasma protein, which may, for example, extend the in vivo plasma half-life of the polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they comprise, or they may contain more than one polypeptide agent.

The candidate polypeptide agent may be produced from eukaryotic produced by prokaryotic cells, it may be further processed by unfolding, e.g. heat denaturation, DTT reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine. The polypeptides may have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

Alternatively, the candidate polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Alternatively, the candidate polypeptide agent may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of cell samples, usually in conjunction with cells not contacted with the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the selected parameters. For example, immunoprecipitation and Western blotting with phospho-specific antibodies or protein arrays may be employed to measure phosphorylation of a Miro protein, a TRAK protein or khc. Similarly, immunoprecipitation and Western blotting with anti-ubiquitin antibodies may be employed to measure the ubiquitination of a Miro protein, a TRAK protein or khc. Live cell imaging may be employed to assay mitochondrial transport, e.g. using a tagged protein, e.g. a fluorescently tagged protein, which localizes to mitochondria. Co-immunoprecipitation or affinity purification techniques may be employed to detect the formation of complexes between Miro, TRAK, and khc. Such methods would be well known to one of ordinary skill in the art.

Kits

Also provided are reagents, devices and kits thereof for practicing one or more of the above-described methods. The subject reagents, devices and kits thereof may vary greatly. Reagents and devices of interest include those mentioned above with respect to the methods of treating a mitochondrial disease in a subject.

In one embodiment, the kit includes one or more of the mitochondrial transport inhibitors provided herein and a pharmaceutically acceptable carrier. In particular embodiments, the mitochondrial transport inhibitor and the pharmaceutically acceptable carrier are packaged separately. For example, the inhibitor may be included in the kit in a dry form, packaged in a container or vial, separate from the carrier. In other embodiments, the inhibitor is formulated in a pharmaceutically acceptable carrier.

In certain embodiments, the kit further includes at least one additional therapeutic agent. In particular embodiments, the additional therapeutic agent is selected from the group consisting of levodopa, a dopamine agonist, a MAO-B inhibitor, amantadine, an anticholinergic, a PUM1 antagonist, an SR protein antagonist, a Parkin agonist, a PINK1 agonist, an 4E-BP1 agonist, a Drp1 agonist, an Atg1 agonist, a TauS2A agonist, a Rbf1 agonist, a Dp antagonist, an E2f1 antagonist, a Polo-like kinase 2 antagonist and a Notch agonist.

In addition to the above components, the subject kits will further include instructions for practicing the subject methods (e.g., instructions regarding route of administration, dose, dosage regimen, site of administration, and the like). These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

PD is a neurodegenerative disorder characterized by the dysfunction and loss of dopaminergic (DA) neurons in the substantia nigra, although neurons in other brain regions are affected as well. Mutations in PINK1 and Parkin are linked to familial forms of early-onset PD (Kitada T., Asakawa, et al. Mutations in the parkin gene cause autosomal recessive juvenile parkinsonism. Nature. 1998; 392:605-608; Valente E. M., et al. Hereditary early-onset Parkinson's disease caused by mutations in PINK1. Science. 2004; 304:1158-1160). PINK1 encodes a Ser/Thr kinase with a mitochondrial targeting sequence, whereas Parkin encodes an E3 ubiquitin ligase. Studies in *Drosophila* first revealed that PINK1 and Parkin act in a common pathway to impact mitochondrial function and DA neuron maintenance (Park J., et al. Mitochondrial dysfunction in *Drosophila* PINK1 mutants is complemented by parkin. Nature. 2006; 441: 1157-1161; Clark I. E., et al. *Drosophila* pink1 is required for mitochondrial function and interacts genetically with parkin. Nature. 2006; 441: 1162-1166; Yang Y., et al. Mitochondrial pathology and muscle and dopaminergic neuron degeneration caused by inactivation of *Drosophila* Pink1 is rescued by Parkin. Proc Natl Acad Sci USA. 2006; 103: 10793-10798; Wang D., et al. Antioxidants protect PINK1-dependent dopaminergic neurons in *Drosophila*. Proc Natl Acad Sci USA. 2006; 103: 13520-13525), in part through the regulation of mitochondrial fission/fusion dynamics (Yang Y., et al. Pink1 regulates mitochondrial dynamics through interaction with the fission/fusion machinery. Proc Natl Acad Sci USA. 2008; 105: 7070-7075; Poole A. C., et al. The PINK1/Parkin pathway regulates mitochondrial morphology. Proc Natl Acad Sci USA. 2008; 105: 1638-1643; Deng H., et al. The Parkinson's disease genes pink1 and parkin promote mitochondrial fission and/or inhibit fusion in *Drosophila*. Proc Natl Acad Sci USA. 2008; 105:14503-14508; Lu B., et al. *Drosophila* models of neurodegenerative diseases. Annu Rev Pathol. 2009; 4:315-342; Whitworth A. J., et al. The PINK1/Parkin pathway: a mitochondrial quality control system? J Bioenerg Biomembr. 2009; 41:499-503). At least in primary cultured mammalian hippocampal neurons and DA neurons, PINK1 and Parkin have been shown to exert similar effects on mitochondrial dynamics as seen in *Drosophila* DA neurons (Yang Y., et al. Pink1 regulates mitochondrial dynamics through interaction with the fission/fusion machinery. Proc Natl Acad Sci USA. 2008; 105: 7070-7075; Yu W., et al. The PINK1/Parkin pathway regulates mitochondrial dynamics and function in mammalian hippocampal and dopaminergic neurons. Hum Mol Genet. 2011; 20: 3227-3240). PINK1 and Parkin are also implicated in mitochondrial quality control (Narendra D., et al. Parkin is recruited selectively to impaired mitochondria and promotes their autophagy. J Cell Biol. 2008; 183:795-803). Decreased mitochondrial membrane potential stabilizes the normally labile PINK1, which recruits Parkin to damaged mitochondria, leading to ubiquitination of mitochondrial proteins and marking damaged mitochondria for removal by autophagy (Geisler S., et al. PINK1/Parkin-mediated mitophagy is dependent on VDAC1 and p62/SQSTM1. Nat Cell Biol. 2010; 12: 119-131). Both mitochondrial fission/fusion dynamics and autophagy are considered important aspects of the mitochondrial quality control mechanism that mediates PINK1/Parkin function in DA neuron maintenance (Whitworth A. J., et al. The PINK1/Parkin pathway: a mitochondrial quality control system? J Bioenerg Biomembr. 2009; 41: 499-503; Youle R. J., et al. Mechanisms of mitophagy. Nat Rev Mol Cell Biol. 2011; 12: 9-14; Chu C. T. A pivotal role for PINK1 and autophagy in mitochondrial quality control: implications for Parkinson disease. Hum Mol Genet. 2010; 19:R28-37; Imai Y. Mitochondrial dynamics and mitophagy in Parkinson's disease: disordered cellular power plant becomes a big deal in a major movement disorder. Curr Opin Neurobiol. 2011; 21: 935-941).

In some PINK1- or Parkin-linked PD patients, symptoms of peripheral neuropathy were also reported (Tassin J., et al. Chromosome 6-linked autosomal recessive early-onset Parkinsonism: linkage in European and Algerian families, extension of the clinical spectrum, and evidence of a small homozygous deletion in one family. The French Parkinson's Disease Genetics Study Group, and the European Consortium on Genetic Susceptibility in Parkinson's Disease. Am J Hum Genet. 1998; 63: 88-94; Bonifati V., et al. Early-onset parkinsonism associated with PINK1 mutations: frequency, genotypes, and phenotypes. Neurology. 2005; 65: 87-95; Abbruzzese G., et al. Does parkin play a role in the peripheral nervous system? A family report. Mov Disord. 2004; 19: 978-981). It is not clear whether this is caused by defects in the aforementioned functions or some other unknown function of PINK1/Parkin. Peripheral neuropathy is a clinical term used to describe various forms of damages to nerves of the peripheral nervous system by distinct mechanisms (Baloh R. H. Mitochondrial dynamics and peripheral neuropathy. Neuroscientist. 2008; 14: 12-18). Many types of peripheral neuropathy are dependent on the length of neuronal axon, with neurons carrying long axons frequently affected.

The fruit fly *Drosophila melanogaster* has served as an excellent model for studying neurodegenerative diseases (Lu B., et al. *Drosophila* models of neurodegenerative diseases. Annu Rev Pathol. 2009; 4:315-342). It was in *Drosophila* that the in vivo function of PINK1 was first revealed (Park J., Lee, et al. Mitochondrial dysfunction in *Drosophila* PINK1 mutants is complemented by parkin. Nature. 2006; 441: 1157-1161; Clark I. E., et al. *Drosophila* pink1 is required for mitochondrial function and interacts genetically with parkin. Nature. 2006; 441: 1162-1166; Yang Y., et al. Mitochondrial pathology and muscle and dopaminergic neuron degeneration caused by inactivation of *Drosophila* Pink1 is rescued by Parkin. Proc Natl Acad Sci USA. 2006; 103: 10793-10798; Wang D., et al. Antioxidants protect PINK1-dependent dopaminergic neurons in *Drosophila*. Proc Natl Acad Sci USA. 2006; 103: 13520-13525). PINK1 mutant flies exhibit abnormal wing postures, reduced flight ability and thoracic ATP level, degeneration of indirect flight muscle and DA neurons, and male sterility, which are caused by the accumulation of dysfunctional mitochondria, thus suggesting a role of PINK1 in mitochondrial function and/or quality control (Park J., Lee, et al. Mitochondrial dysfunction in *Drosophila* PINK1 mutants is complemented by parkin. Nature. 2006; 441: 1157-1161; Clark I. E., et al. *Drosophila* pink1 is required for mitochondrial function and interacts genetically with parkin. Nature. 2006; 441: 1162-1166; Yang Y., et al. Mitochondrial pathology and muscle and dopaminergic neuron degeneration caused by inactivation of *Drosophila* Pink1 is rescued by Parkin. Proc Natl Acad Sci USA. 2006; 103: 10793-10798; Wang D., et al. Antioxidants protect PINK1-dependent dopaminergic neurons in *Drosophila*. Proc Natl Acad Sci USA. 2006; 103: 13520-13525). Further genetic studies in *Drosophila* have also uncovered important functions of PINK1 in regulating mitochondrial morphology and electron transport chain activity (Yang Y., et al. Pink1 regulates mitochondrial dynamics through interaction with the fission/fusion machinery. Proc Natl Acad Sci USA. 2008; 105: 7070-7075; Poole A. C., et al. The PINK1/Parkin pathway regulates mitochondrial morphology. Proc Natl Acad Sci USA. 2008; 105: 1638-1643; Deng H., et al. The Parkinson's disease genes pink1 and parkin promote mitochondrial fission and/or inhibit fusion in *Drosophila*. Proc Natl Acad Sci USA. 2008; 105:14503-14508; Liu W., et al. Pink1 regulates the oxidative phosphorylation machinery via mitochondrial fission. Proc Natl Acad Sci USA. 2011; 108: 12920-12924).

The power of the *Drosophila* neurodegenerative disease model lies in the ability to facilitate unbiased genetic modifier screens to identify new players involved in the disease process. Using this approach, it is shown below that PINK1 genetically interacts with the mitochondrial transport machinery. A major aspect of axonal transport is mediated by mitochondrial transport machinery, including motor proteins that travel on axonal microtubules, which are polarized and uniformly orientated with their plus-ends pointing towards nerve terminals. The kinesin and dynein motors are involved in microtubule plus-end (anterograde) and minus-end directed (retrograde) transport, respectively (Hirokawa N. Kinesin and dynein superfamily proteins and the mechanism of organelle transport. Science. 1998; 279: 519-526). Mitochondria are mainly produced in neuronal cell body and delivered to sites where metabolic demand is high, such as the synapses and nodes of Ranvier (Hollenbeck P. J., et al. The axonal transport of mitochondria. J Cell Sci. 2005; 118:5411-5419). The functions of Mitochondrial Rho (Miro), a mitochondrial outer membrane GTPase, and the cytosolic protein Milton are critical for mitochondrial transport, as they serve to link mitochondria with kinesin motors and the microtubule cytoskeleton (Guo X., et al. The GTPase dMiro is required for axonal transport of mitochondria to *Drosophila* synapses. Neuron. 2005; 47: 379-393; Stowers R. S., et al. Axonal transport of mitochondria to synapses depends on milton, a novel *Drosophila* protein. Neuron. 2002; 36: 1063-1077).

As shown below, reduction of function in Miro, Milton, or kinesin heavy chain effectively rescued the PINK1 mutant phenotypes. Conversely, overexpression (OE) of Miro led to the formation of enlarged mitochondria and resulted in DA neuron loss, thus phenocopying PINK1 mutants. By monitoring mitochondrial movement in live *Drosophila* larval motor neurons, which possesses long axons and could serve as a model system for studying peripheral neuropathy, it is shown that PINK1 directly regulates mitochondrial transport. The function of PINK1 in mitochondrial transport may contribute to PD pathogenesis in DA neurons and underlie the peripheral neuropathy symptoms associated with certain PINK1 mutations in some PD patients.

The biochemical analysis provided herein demonstrate that overexpressed PINK1 in cooperation with Parkin could regulate Miro protein ubiquitination and stability, which contributes to the regulatory effect of PINK1 on mitochondrial motility.

Materials and Methods

Fly Strains and Reagents.

Flies were raised according to standard procedures at indicated temperatures. Sources of fly strains and other reagents are as follows: dPINK1B9: Dr. J. Chung (Park J., Lee, et al. Mitochondrial dysfunction in *Drosophila* PINK1 mutants is complemented by parkin. Nature. 2006; 441: 1157-1161); UAS-dMiro and anti-dMiro antibody: Dr. K. Zinsmaier (Guo X., et al. The GTPase dMiro is required for axonal transport of mitochondria to *Drosophila* synapses. Neuron. 2005; 47: 379-393); TH-GAL4, UAS-PINK1, UAS-PINK1 RNAi and rabbit anti-*Drosophila* TH antibody: described before (Yang Y., et al. Mitochondrial pathology and muscle and dopaminergic neuron degeneration caused by inactivation of *Drosophila* Pink1 is rescued by Parkin. Proc Natl Acad Sci USA. 2006; 103: 10793-10798); UAS-Miro RNAP[106683]: Vienna *Drosophila* RNAi Center; UAS-Miro RNAi[27695], UAS-Milton RNAi[28385] and UAS-Khc RNAi[25898]: Harvard Transgenic RNAi Project (TRiP) and Bloomington *Drosophila* Stock Center; all other fly lines: Bloomington *Drosophila* Stock Center; FLAG-hParkin mutants and HA-ubiquitin: Drs. N. Matsuda, K. Tanaka and S. Hatakeyama; Myc-hMiro1 and Myc-hMiro2 plasmids: Dr. P. Aspenström (Fransson A., et al. Atypical Rho GTPases have roles in mitochondrial homeostasis and apoptosis. J Biol Chem. 2003; 278: 6495-6502); hPINK1 cDNAs were cloned into pcDNA3-FLAG vector.

Antibodies used in this study are as follows: anti-RHOT1/Miro1 (4H4, Abnova), anti-RHOT2/Miro2 (Protein technology Group), anti-PINK1 (Novus), anti-Parkin (PRK8, Santa Cruz Biotechnology), anti-Tom20 (FL-145, Santa Cruz Biotechnology), anti-VDAC1 (Abcam), anti-OXPHOS Complex IV subunit I/COX I (Invitrogen), anti-Tim23 (BD), anti-NDUFA9 (Invitrogen), anti-Cytochrome c (BD), anti-HtrA2/Omi (as described in (Suzuki Y., et al. A serine protease, HtrA2, is released from the mitochondria and interacts with XIAP, inducing cell death. Mol Cell. 2001; 8: 613-621)), anti-Hsp60 (BD), anti-PDHA1 (Abcam), anti-HA (3F10, Roche), anti-Myc (4A6, Millipore; #2272, Cell Signaling Technology), anti-β-actin (AC-15, Sigma-Aldrich), anti-α-tubulin (DM1A, Millipore), Peroxidase anti-Guinea Pig IgG antibody (Jackson ImmunoResearch), Texas Red-conjugated anti-HRP (Jackson ImmunoResearch), Alexa Fluor 488 nm-conjugated goat anti-chicken IgG (Invitrogen) and Alexa Fluor 594 nm-conjugated goat anti-rabbit IgG (Invitrogen).

Fly Wing Posture, Behavior, ATP Measurement, and Immunohistochemistry.

These assays were carried out essentially as described before (Liu S., et al. Reduction of Protein Translation and Activation of Autophagy Protect against PINK1 Pathogenesis in *Drosophila melanogaster*. PLoS Genet. 2010; 6: e1001237). The thoracic ATP level was measured using a luciferase based bioluminescence assay (ATP Bioluminescence Assay Kit HS II, Roche applied science) as described (Liu S., et al. Reduction of Protein Translation and Activation of Autophagy Protect against PINK1 Pathogenesis in *Drosophila melanogaster*. PLoS Genet. 2010; 6: e1001237).

Whole-mount brain immunohistochemistry for TH and mitoGFP was performed as described previously (Liu S., et al. Reduction of Protein Translation and Activation of Autophagy Protect against PINK1 Pathogenesis in *Drosophila melanogaster*. PLoS Genet. 2010; 6: e1001237). For DA neuron mitochondrial morphology analysis, mitoGFP was expressed in *Drosophila* DA neurons using the TH-Gal4 driver. Brains from 3-day-old adult flies of the indicated genotypes were immunostained with the anti-TH antibody to label DA neuron and anti-GFP antibody to label mitochondria. For measurement of mitochondrial size distribution, the size of each mitochondrial aggregate was represented by the length of its longest axis. The percentage of DA neurons in the PPL1 cluster that have one or more mitochondria exceeding the indicated size was shown. Six flies of each genotype were used for the analysis.

Live Imaging of Mitochondrial Movement.

The motor neuron-specific OK6-Gal4 driver was used to express UAS-mitoGFP in the larval segment neurons, and 3rd instar male larvae raised at 29° C. were used for live imaging. Larvae were briefly washed with water and anesthetized for 4 min in 1.5 ml eppendorf tubes containing 4 µl suprane (Baxter International Inc.), before being placed ventral side up into a small chamber. The chamber was created on glass slide with double-sided tape and cover glass. Additional suprane (4 µl) was introduced into the chamber before it was sealed with Valap (1:1:1 amount of vaseline, lanolin, paraf in wax). Mitochondria were viewed with an upright Leica DM6000 B microscope equipped with a laser scanner and a 63× oil-immersion objective. Larvae were positioned to have their ventral ganglion (VG) appearing on the right of the acquired image and segmental nerves aligned horizontally across the image. Before recording mitochondrial movement, a centered region of 1024×200 pixel (61.5 µm×12.0 µm, 4× digital zoom) close to the VG was photobleached for 30 with 488 nm excitation argon laser set at 80% output power. The viewing field was then zoomed out (2.5× digital zoom) and mitochondrial movement was immediately recorded by time-lapse video (2 s/frame, 300 s total) in a region of 1024×150 pixel (98.4 µm×14.4 µm) with the laser power reduced to 10% of the maximum output. The pinhole was set at 200 µm for all the experiments. Time-lapse images were acquired within 30 min of anesthetization. Mitochondrial flux was calculated by normalizing the number of mitochondria that passes certain point within the time frame examined. Mitochondrial net velocity was calculated by normalizing mitochondrial net displacement with time. At least 5 larvae of each genotype were analyzed.

Cell Culture and Transfection.

HeLa cells were maintained at 37° C. with 5% $CO_2$ atmosphere in DMEM (Wako) supplemented with 10% FCS (GIBCO) and non-essential amino acids (Invitrogen). Plasmids and siRNA duplexes (Invitrogen) were transfected using Lipofectamine 2000 (Invitrogen) and Lipofectamine RNAiMAX (Invitrogen), respectively, according to manufacturer's instructions. To depolarize the mitochondria, HeLa cells were treated with 10 µM CCCP (Sigma-Aldrich) at 36 hr (for plasmids) or 72 hr (for siRNA) post-transfection.

The S156A mutations were introduced into human Miro1 and Miro2 by PCR-based mutagenesis using the following primers: For hMiro1, Forward primer: 5'-GCA gag ctcttttatt acgcac-3' (SEQ ID NO: 3); Reverse primer: 5'-tatg ttcttcaggt ttttcgc-3' (SEQ ID NO: 4). For hMiro2, Forward primer: 5'-GCA gagct gttctactac gc-3' (SEQ ID NO: 5); Reverse primer: 5'-ga tgttcctcag gttcttggc-3' (SEQ ID NO: 6). Full-length sequences of hMiro1 S156A and hMiro2 S156A were confirmed by sequencing.

Immunoblotting, Immunoprecipitation, and In Vitro Phosphorylation.

For brain extract preparation, 6 fly heads were quickly dissected and homogenized in 60 µl SDS-PAGE sample buffer. 5 µl brain extracts from each genotype were loaded onto SDS-PAGE gel. Guinea pig anti-dMiro antibody (120000) and Peroxidase Anti-Guinea Pig IgG antibody (110000, Jackson ImmunoResearch Labs) were used for Western Blot. For HeLa cell-based biochemical analysis, cells were lysed in 1% Triton X-100-based lysis buffer (10 mM Tris-HCl [pH 7.6], 120 mM NaCl, 5 mM EDTA, 1% Triton X-100 and protease inhibitor [Nacalai Tesuque]). Immunoprecipitation was performed using Immunoprecipitation Kit-Dynabeads Protein G (Invitrogen) according to manufacturer's instructions.

In vitro kinase assay was performed essentially as described (Imai Y., et al. The loss of PGAM5 suppresses the mitochondrial degeneration caused by inactivation of PINK1 in Drosophila. PLoS Genet. 2010; 6: e1001229), using a 2×GST-dPINK1 fusion protein with GST fused at both the N- and C-terminus of dPINK1 as the kinase source and a GST-dMiroΔTM fusion protein as the substrate. GST-dMiroΔTM covers amino acids 1-634 of the full-length dMiro protein. The GST-dMiro-LTM plasmid was constructed by amplifying a Myc-tagged dMiro fragment without the transmembrane domain from a pUAST-Myc-dMiro plasmid using 5'-CGCCCG-GGTGAGCAGAAACTCATCTCTGAA-GAAG-3' (SEQ ID NO:1) and 5'-ATGCGGCCGCTACT-TGGG-GTCCTCCGTC-ATC-3' (SEQ ID NO:2) as primers. The amplified fragment was inserted into the SmaI and NotI cloning sites of the pGEX-6P-1 vector. Recombinant GST fusion proteins were purified from bacteria according to standard protocols.

Immunocytochemistry.

Cells were fixed with 4% paraformaldehyde in PBS and permeabilized with 0.2% Triton X-100 (for mitophagy in FIG. 6C) or 0.5% Triton X-100 (for mitochondrial morphology in FIG. 6B) in PBS. Cells stained with the appropriated antibodies and counterstained with DAPI were imaged using a laser-scanning microscope (LMS510 META; Carl Zeiss, Inc.) with a Plan-Apochromat 63×NA1.4 or 100×/1.4 Oil differential interference contrast objective lens. Image contrast and brightness were adjusted in Image Browser (Carl Zeiss, Inc.)

Statistical Analysis.

Two-tailed Student's t tests were used for statistical analysis. p values of <0.05, <0.01, and <0.005 were indicated with one, two, and three asterisks (*), respectively.

Results

Genetic Interaction Between PINK1 and the Mitochondrial Transport Machinery.

By taking advantage of the easily identifiable phenotype of abnormal wing posture induced by dPINK1 inactivation, a genetic screen was performed for modifiers of PINK1. The scheme was similar as described before (Liu S., et al. Reduction of Protein Translation and Activation of Autophagy Protect against PINK1 Pathogenesis in Drosophila melanogaster. PLoS Genet. 2010; 6: e1001237). In this screen, components of the mitochondrial transport machinery were identified as genetic modifier of PINK1. Knockdown of Miro, Milton or Kinesin heavy chain (Khc) each rescued the muscle phenotypes in PINK1$^{B9}$ null mutant, including abnormal wing posture, decreased fly ability and ATP depletion (FIG. 1A-1C). Conversely, overexpression (OE) of Miro and Khc enhanced such phenotypes (FIG. 1A-1C). These results demonstrated strong genetic interaction between PINK1 and the mitochondrial transport machinery as a whole, supporting that mitochondrial transport is the underlying mechanism mediating their genetic interaction.

Genetic Interaction Between Miro and PINK1 in the PD-Relevant DA Neurons.

Figure 2:
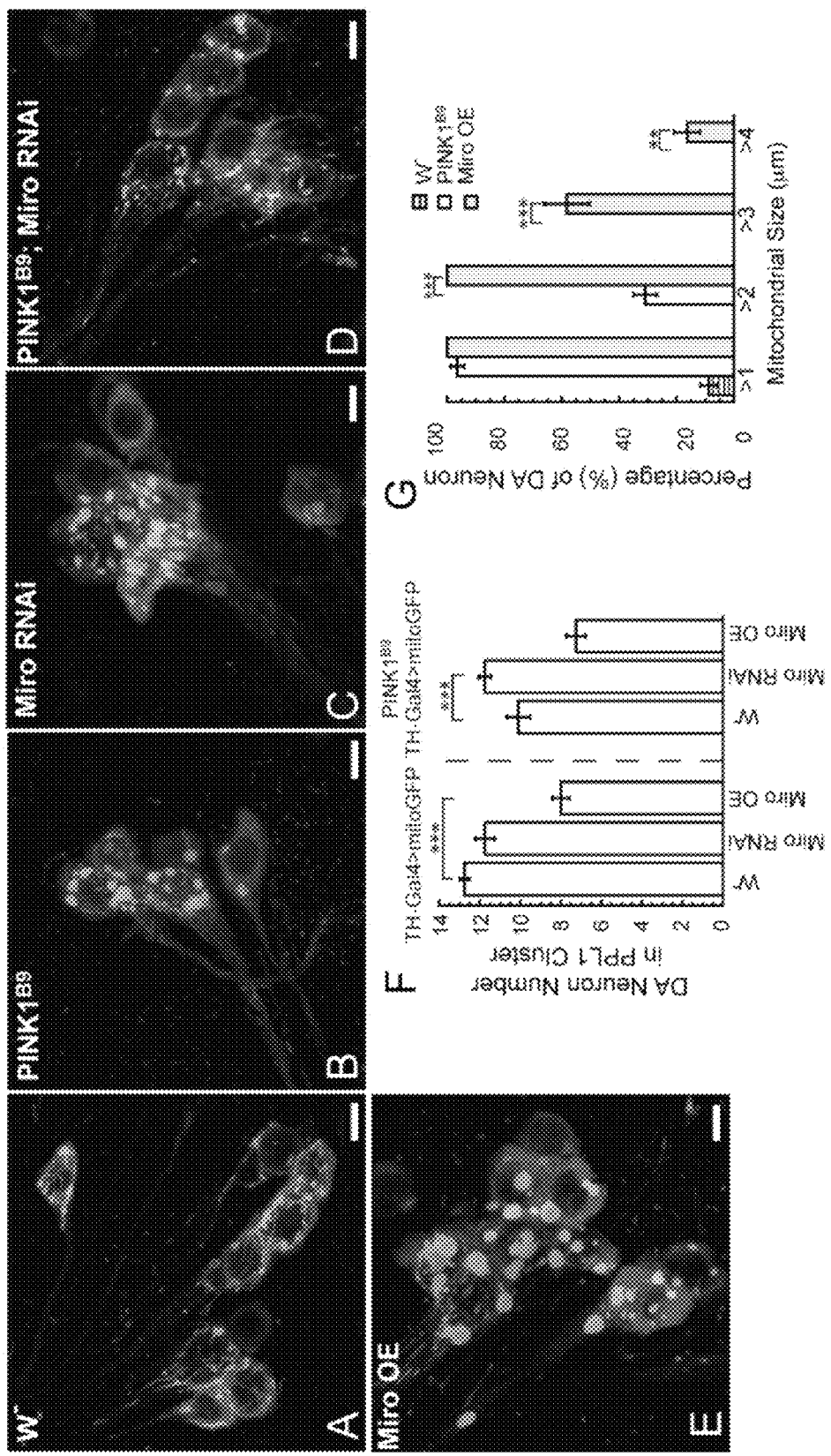
FIG. 2. Genetic interaction between PINK1 and Miro in DA neurons. (A-E) Mitochondrial morphology in DA neurons of different genotyped flies visualized with mitoGFP expressed under TH-Gal4 control. Red: TH, green: GFP. DA neurons of the protocerebral posterior lateral 1 (PPL1) cluster were shown. Scale bar: 5 μm. (F) Effects of Miro-RNAi and Miro-OE on DA neuron maintenance in wild type and PINK1$^{B9}$ mutant backgrounds. DA neuron number was scored in 14-day old flies. At least 5 flies were used for each genotype. (G) Mitochondrial-size distribution in DA neurons of the various genotyped flies. Data are presented as mean±s.e.m.

To test the relevance of the functional interaction between PINK1 and the mitochondrial transport machinery to PD pathogenesis, PINK1/mitochondrial transport machinery interactions were examined in DA neurons, the disease-relevant cell type. As in the muscle, Miro-RNAi effectively rescued PINK1 mutant phenotypes in DA neurons, both in terms of mitochondrial aggregation (FIG. 2A-2D) and DA neuron loss (FIG. 2F). Moreover, Miro-OE alone, driven by the TH-Gal4 driver, caused aberrant mitochondrial aggregation (2E, 2G) and DA neuron loss (FIG. 2F), thus phenocopying PINK1 loss-of-function effects (FIG. 2B, 2F, 2G), although the Miro-OE effect was noticeably stronger than PINK1 mutant. It is worth noting that TH-Gal4-driven Miro-OE in PINK1 mutant background resulted in dramatically reduced viability, although the surviving adults did not show further DA neuron loss than that induced by Miro-OE alone (FIG. 2F). Together, these results demonstrate that PINK1 and Miro also exhibit strong genetic interaction in DA neurons, with decreased dMiro level/activity ameliorating the detrimental effects caused by the loss of dPINK1, whereas increased dMiro level or activity phenocopying dPINK1 mutants.

PINK1 Regulates Mitochondrial Motility in Drosophila Larval Motor Neurons.

The strong genetic interaction between PINK1 and Miro raised the interesting possibility that PINK1 might directly regulate mitochondrial transport, the impairment of which might contribute to PINK1-related parkinsonism. This was further supported by the DA neuron loss induced by Miro-OE alone, which acted by altering mitochondrial transport. To confirm this, the effect of PINK1 on mitochondrial movement in *Drosophila* larval motor neurons was examined. *Drosophila* larval motor neurons provide a system amenable to live imaging of mitochondrial transport. Mitochondrially-targeted GFP (mitoGFP) expressed specifically in motor neurons was used to track mitochondrial movement via live imaging in anesthetized third instar larvae (FIG. 3A), using well-established procedures (Pilling A. D., et al. Kinesin-1 and Dynein are the primary motors for fast transport of mitochondria in *Drosophila* motor axons. Mol Biol Cell. 2006; 17: 2057-2068) (Russo G. J., et al. *Drosophila* Miro is required for both anterograde and retrograde axonal mitochondrial transport. J. Neurosci. 2009; 29: 5443-5455). To highlight the mitochondria undergoing active transport, a 61.5 µm-long segment of motor neuron was photobleached and the movement of fluorescently labeled mitochondria moving into the bleached area from both directions was recorded at 1 frame/2 s for 300 s (FIG. 3B). From these videos, mitochondrial flux (the normalized number of mitochondria that passes certain point over time), mitochondrial net velocity (the normalized mitochondrial net displacement over time), and mitochondrial morphology (e.g. mitochondrial length) in different genetic backgrounds were analyzed. In general, mitochondrial net velocity is controlled primarily by the intrinsic properties and quantities of motor proteins associated with the mitochondria (Russo G. J., et al. *Drosophila* Miro is required for both anterograde and retrograde axonal mitochondrial transport. J Neurosci. 2009; 29: 5443-5455), while mitochondrial flux can also be significantly affected by mitochondrial morphology, as changes in mitochondrial morphological features such as length can increase or decrease the number of motile mitochondria.

It was found that PINK1-OE decreased mitochondrial flux as well as net velocity in both anterograde and retrograde directions, similar to the effect of Miro-RNAi, although the PINK1-OE effect appeared to be slightly weaker (FIG. 3B-3D; Videos S1, S2, S4). In contrast, PINK1-RNAi and Miro-OE both increased the net velocity of anterograde mitochondrial transport, with retrograde transport largely unaffected (FIG. 3B, 3C). PINK1-RNAi also increased anterograde mitochondrial flux (FIG. 3C), while mitochondrial flux in Miro-OE background was reduced in both anterograde and retrograde directions (FIG. 3C). The reduction of mitochondrial flux by Miro-OE could be partially explained by the formation of very long mitochondria in Miro-OE motor neurons (FIG. 3E, 3F), as previously observed (Russo G. J., et al. *Drosophila* Miro is required for both anterograde and retrograde axonal mitochondrial transport. J Neurosci. 2009; 29: 5443-5455).

In addition to mitochondrial motility, PINK1 also affected mitochondrial length in motor neurons. PINK1-RNAi increased mitochondrial length in the axons of larval motor neurons as in Miro-OE case, although the effect of Miro-OE was stronger. Conversely, PINK1-OE and Miro-RNAi both decreased mitochondrial length (FIG. 3E, 3F). To address whether PINK1-induced mitochondrial motility change was due to its effect on mitochondrial length, mitochondrial transport in genetic backgrounds were examined, where mitochondrial fusion/fission machinery was directly manipulated to alter mitochondrial length. Increasing mitochondrial fission by overexpression of the fission protein Fis1 or knockdown of the fusion protein Marf led to decreased mitochondrial length (FIG. 3E, 3F), similar to the effects of Miro-RNAi or PINK1-OE. However, in contrast to the decreased mitochondrial flux and net velocity as observed in the Miro-RNAi or PINK1-OE backgrounds, Fis1-OE and Marf-RNAi both increased mitochondrial flux and net velocity in anterograde and retrograde directions (FIG. 3B-3D), suggesting that mitochondrial length and transport kinetics are not always directly correlated, which is consistent with a previous report (Russo G. J., et al. *Drosophila* Miro is required for both anterograde and retrograde axonal mitochondrial transport. J Neurosci. 2009; 29: 5443-5455). Collectively, these results support the notion that PINK1 regulates mitochondrial transport and that its effect on mitochondrial motility is direct, rather than a secondary effect of mitochondrial length change.

Altered PINK1 Activities Affect Mitochondrial Distribution in Motor Neuron Axons.

Figure 4:
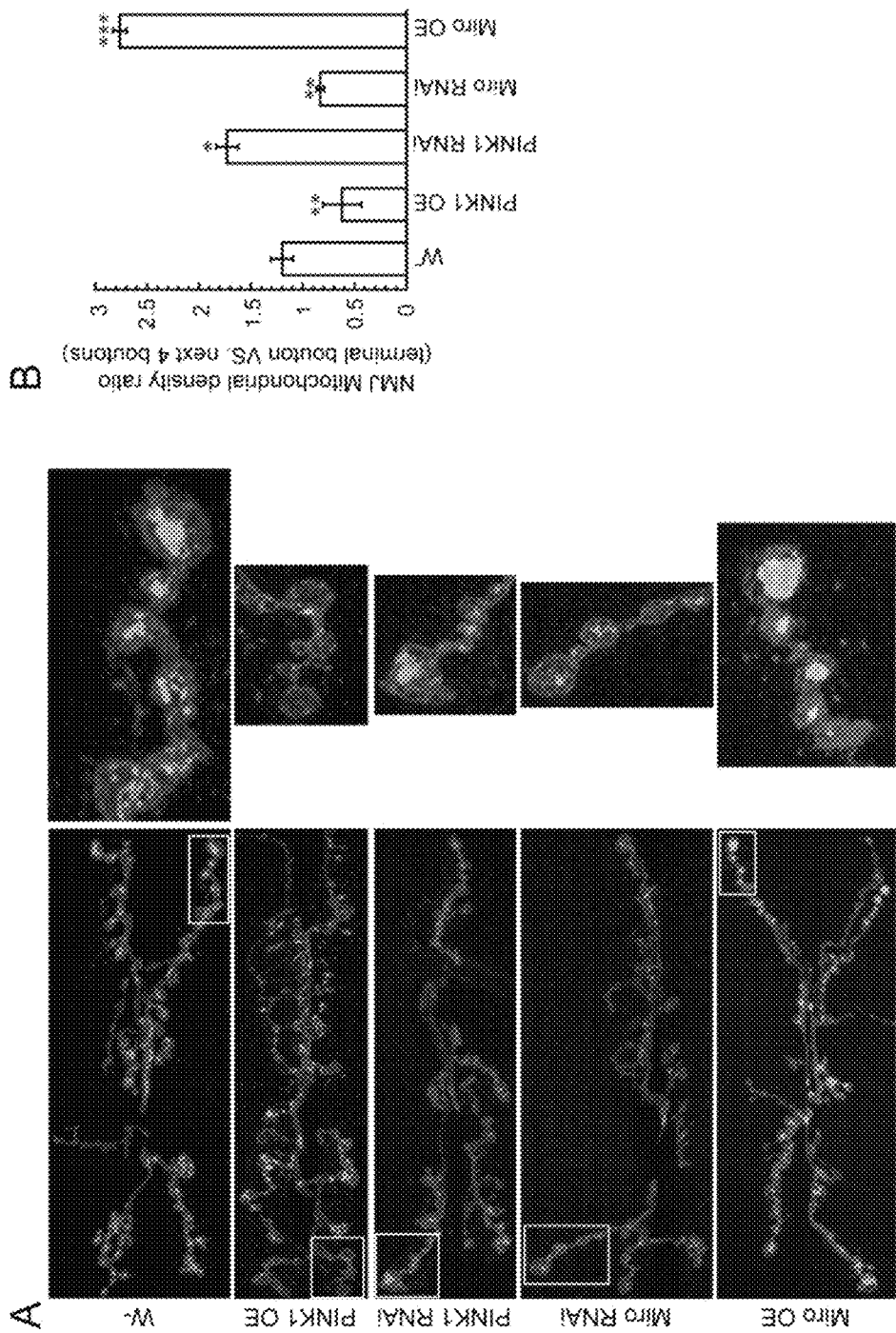
FIG. 4. PINK1 affects mitochondrial distribution within motor neuron nerve terminals at the *Drosophila* larval neuromuscular junction. Pan-neuronal elav-Gal4 driver was used to express mitoGFP in different genetic backgrounds to examine the mitochondrial distribution at the neuromuscular junction (NMJ) of muscle 6/7 in A3-A4 segments. Anti-GFP antibody (Green) and anti-HRP-Texas Red antibody (Red) were used to visualize mitochondria and boutons, respectively. (A) Representative images of mitochondrial distribution at the NMJs of wild type, PINK1-OE, PINK1-RNAi, Miro-RNAi and Miro-OE flies were shown in the left panels. Detailed mitochondrial distribution of the boxed areas in the left panels was shown in the right panels. (B) PINK1 regulates mitochondrial distribution at the NMJ. Mitochondrial density of each bouton was estimated by its average GFP fluorescence intensity, represented as total GFP green fluorescence (anti-GFP staining) of each bouton/bouton size (HRP-Texas Red staining). Mitochondrial density ratio of the most distal bouton versus the next 4 boutons was used to quantitatively compare mitochondrial distribution at the NMJ. Compared to the control, PINK1 knockdown showed significant accumulation of mitochondria at the most distal bouton, although its effect was not as strong as Miro-OE. In contrast, Miro-RNAi and PINK1-OE both led to reduced mitochondrial mass in the most distal boutons.

In addition to mitochondrial motility, mitochondrial distribution at motor neuron nerve terminals at the larval neuromuscular junction (NMJ) were examined. Such data can be used as an indirect measure of mitochondrial motility. Consistent with a previous report (Guo X., et al. The GTPase dMiro is required for axonal transport of mitochondria to *Drosophila* synapses. Neuron. 2005; 47: 379-393), Miro-OE led to the accumulation of mitochondria in the most distal boutons, which is likely the consequence of net anterograde transport (FIG. 4A, 4B). PINK1 knockdown showed a similar effect (FIG. 4A, 4B). Thus, the dysfunctional mitochondria in PINK1 mutant might gain longer retention time in the distal segment of motor neuron axons where synapses are formed. In contrast, Miro-RNAi and PINK1-OE both led to decreased accumulation of mitochondria in the most distal boutons (FIG. 4A, 4B). As such, PINK1 regulates mitochondrial distribution in motor neuron nerve terminals, through its effect on mitochondrial transport.

Overactivation of the PINK1/Parkin Pathway Reduces Miro Protein Level.

Figure 5A:
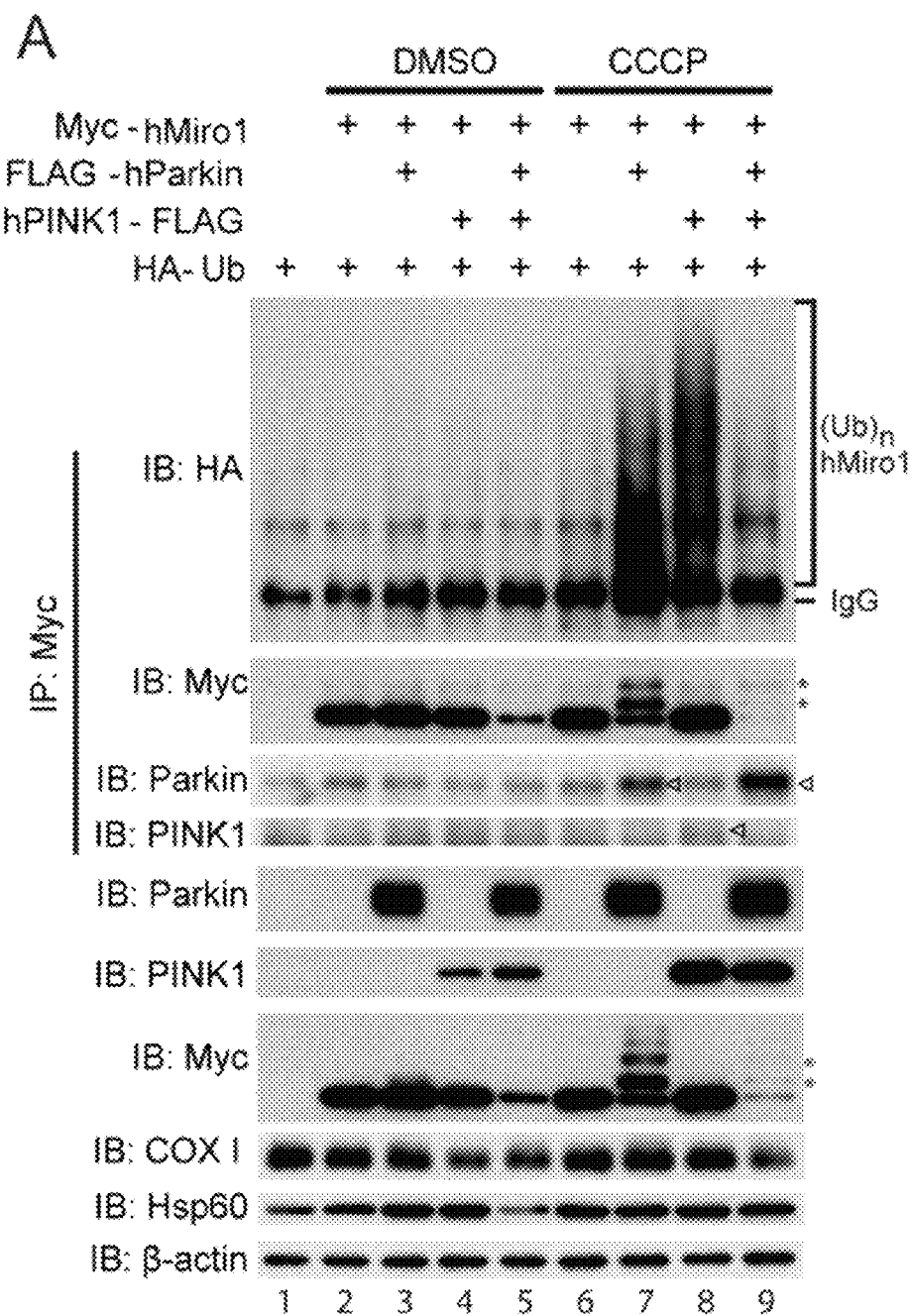
FIG. 5. PINK1/Parkin regulates the ubiquitination and stability of Miro protein. (A) Effects of hPINK1 and hParkin on the ubiquitination and protein stability of exogenous hMiro1 in HeLa cells. Cells transfected with the indicated plasmids were treated with or without 10 μM CCCP for 90 min. Arrowheads, Parkin or PINK1 co-precipitated with hMiro1; Asterisks: oligo-ubiquitinated hMiro1. The inner mitochondrial membrane protein COX I and the mitochondrial matrix protein Hsp60 are used as loading controls for mitochondrial proteins. β-actin serves as a loading control for cytosolic proteins. (B) Effects of mutant hPINK1 or hParkin on hMiro1 protein level in HeLa cells. The Parkin K211N mutation in the linker domain is reported to lack both ubiqutin-ligase (E3) and mitochondrial translocation activities, while the Parkin T415 mutation in the RNIG2 domain, which disrupts E3 activity, retains partial mitochondrial translocation activity (Matsuda N., et al. PINK1 stabilized by mitochondrial depolarization recruits Parkin to damaged mitochondria and activates latent Parkin for mitophagy. J Cell Biol. 2010; 189: 211-221). The PINK1 L347P mutant is reported to have reduced kinase activity (Pridgeon J. W., et al. PINK1 Protects against Oxidative Stress by Phosphorylating Mitochondrial Chaperone TRAP1. PLoS Biol. 2007; 5: e172). An OMM protein VDAC1 is shown as a loading control for mitochondrial proteins. (C, D) Time-course experiments examining the effects of hPINK1/hParkin on the stability of endogenous hMiro1/2 proteins. Specificity of the hMiro antibodies was confirmed using hMiro knockdown cells (C). (E) Endogenous dMiro level in fly brain extracts of the various genetic backgrounds. elav-Gal4 was used to drive the expression of the transgenes. Normalized dMiro level compared to wild type control was shown as mean±s.e.m. (n=3).
Figure 5B:
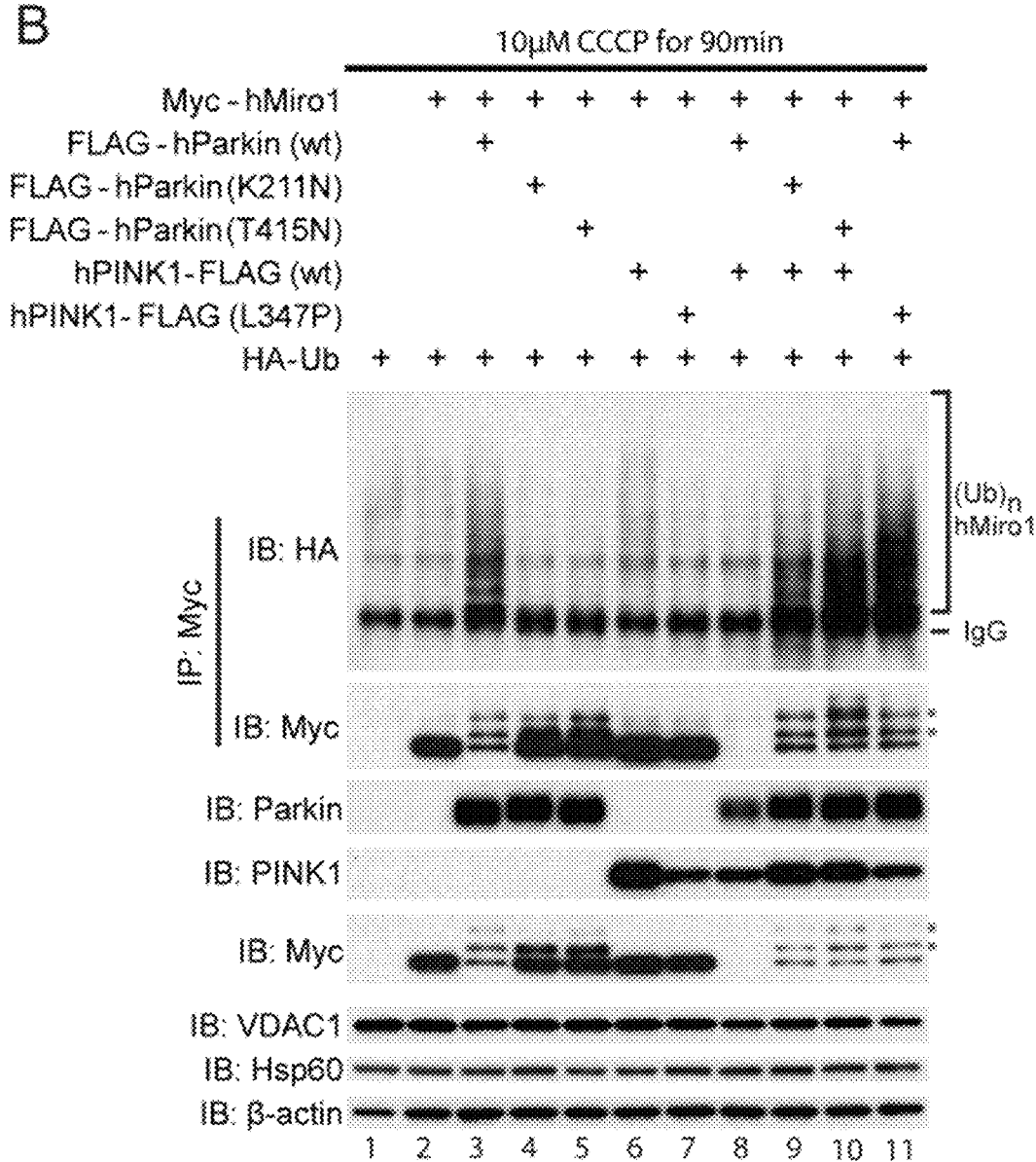

The results described above showed that PINK1 and Miro exert opposite effects on mitochondrial morphology, motility and distribution. The biochemical mechanisms underlying their negative genetic relationship was next explored. HeLa cells were used to test whether Miro protein level might be regulated by PINK1 and possibly Parkin, which tends to work together with PINK1 in a common pathway (Park J., Lee, et al. Mitochondrial dysfunction in *Drosophila* PINK1 mutants is complemented by parkin. Nature. 2006; 441: 1157-1161; Clark I. E., et al. *Drosophila* pink1 is required for mitochondrial function and interacts genetically with parkin. Nature. 2006; 441: 1162-1166; Yang Y., et al. Mitochondrial pathology and muscle and dopaminergic neuron degeneration caused by inactivation of *Drosophila* Pink1 is rescued by Parkin. Proc Natl Acad Sci USA. 2006; 103: 10793-10798; Narendra D. P., et al. PINK1 Is Selectively Stabilized on Impaired Mitochondria to Activate Parkin. PLoS Biol. 2010; 8: e1000298). There are two Miro homologues in human cells, hMiro1 and hMiro2, that are ~60% identical (Fransson A., et al. Atypical Rho GTPases have roles in mitochondrial homeostasis and apoptosis. J Biol Chem. 2003; 278: 6495-6502). Overexpression of either hPINK1 or hParkin did not lead to obvious change of exogenous hMiro1 protein level under normal conditions, but a modest reduction of hMiro1 level was observed when hPINK1 and hParkin were co-expressed (FIG. 5A, lane 5). A decline in mitochondrial membrane-potential induced by the mitochondrial uncoupler carbonyl cyanide m-chlorophenylhydrazone (CCCP) was reported to activate the PINK1/Parkin pathway (Narendra D., et al. Parkin is recruited selectively to impaired mitochondria and promotes their autophagy. J Cell Biol. 2008; 183:795-803; Geisler S., et al. PINK1/Parkin-mediated mitophagy is dependent on VDAC1 and p62/SQSTM1. Nat Cell Biol. 2010; 12: 119-131; Narendra D. P., et al. PINK1 Is Selectively Stabilized on Impaired Mitochondria to Activate Parkin. PLoS Biol. 2010; 8: e1000298). Under CCCP treatment condition, hPINK1 or hParkin each significantly stimulated hMiro1 ubiquitination (FIG. 5A). Since HeLa cells express very little endogenous Parkin (Narendra D., et al. Parkin is recruited selectively to impaired mitochondria and promotes their autophagy. J. Cell Biol. 2008; 183:795-803), the effect of hPINK1 alone on hMiro1 ubiquitination (FIG. 5A, lane 8) suggested that other E3 ligase(s) might be recruited by hPINK1 to ubiquitinate hMiro1. However, this ubiquitination event did not appear to lead to destabilization of hMiro1 (FIG. 5A, IB: Myc). In contrast, coexpression of hPINK1 and hParkin dramatically reduced hMiro1 level in the presence of CCCP (FIG. 5A, lanes 9). Importantly, pathogenic mutations in hPINK1 or hParkin abolished this effect (FIG. 5B, lanes 4 and 5 compared with lane 3, and lanes 9-11 compared with lane 8), indicating that functional hPINK1 and hParkin are both required in the destabilization of hMiro1. Previously, many outer mitochondrial membrane (OMM) proteins were shown to be degraded by the ubiquitin proteasome system (UPS) pathway in a PINK1/Parkin-dependent reaction at an early step of mitophagy, while other OMM proteins might be eliminated by subsequent autophagosome-dependent events (Chan N. C., et al. Broad activation of the ubiquitin-proteasome system by Parkin is critical for mitophagy. Hum Mol Genet. 2011; 20: 1726-37) (Yoshii S. R, et al. Parkin Mediates Proteasome-dependent Protein Degradation and Rupture of the Outer Mitochondrial Membrane. J Biol Chem. 2011; 286: 19630-19640). Thus, direct or indirect substrates of PINK1/Parkin could be distinguished by their degradation kinetics (Chan N. C., et al. Broad activation of the ubiquitin-proteasome system by Parkin is critical for mitophagy. Hum Mol Genet. 2011; 20: 1726-37). In these experiments, hMiro1 was more rapidly degraded than another OMM protein VDAC1 (FIG. 5B, VDAC1), a reported Parkin substrate involved in mitophagy (Geisler S., et al. PINK1/Parkin-mediated mitophagy is dependent on VDAC1 and p62/SQSTM1. Nat Cell Biol. 2010; 12: 119-131), supporting that hMiro1 is a direct substrate of Parkin.

Similar to hMiro1, hMiro2 could also be ubiquitinated by PINK1 and Parkin co-expression or after CCCP treatment. However, the degradation of hMiro2 was at a slower rate compared to hMiro1, consistent with a previous result (Chan N. C., et al. Broad activation of the ubiquitin-proteasome system by Parkin is critical for mitophagy. Hum Mol. Genet. 2011; 20: 1726-37). Furthermore, like exogenous hMiro1, endogenous hMiro1 was also rapidly degraded by PINK1/Parkin overexpression in HeLa cells and its level was dramatically reduced within 15 min of CCCP treatment. The degradation of endogenous hMiro2 was again at a slower rate than that of hMiro1 (FIG. 5C, 5D).

The effect of the PINK1/Parkin pathway on Miro protein level in an in vivo setting was next examined. Similar to the results in HeLa cells, Drosophila dMiro protein level was decreased in the brain extracts of PINK1 or Parkin overexpression adult flies (FIG. 5E). Conversely, dMiro level was increased in PINK1$^{B9}$ mutant brain extracts (FIG. 5E). These results are consistent with dPINK1 negatively regulating dMiro protein level in vivo. It is worth noting that different from the effects seen in HeLa cells, overexpression of PINK1 or Parkin alone was sufficient to reduce dMiro level in adult Drosophila brain, and the co-expression of PINK1 and Parkin did not lead to further reduction of dMiro level than PINK1-OE alone, indicating that the endogenous levels or activities of PINK1 and Parkin are already sufficient to support each others action in the Drosophila brain.

Knockdown of Miro Promotes the Removal of Damaged Mitochondria by Parkin-Mediated Mitophagy.

Figure 6A:
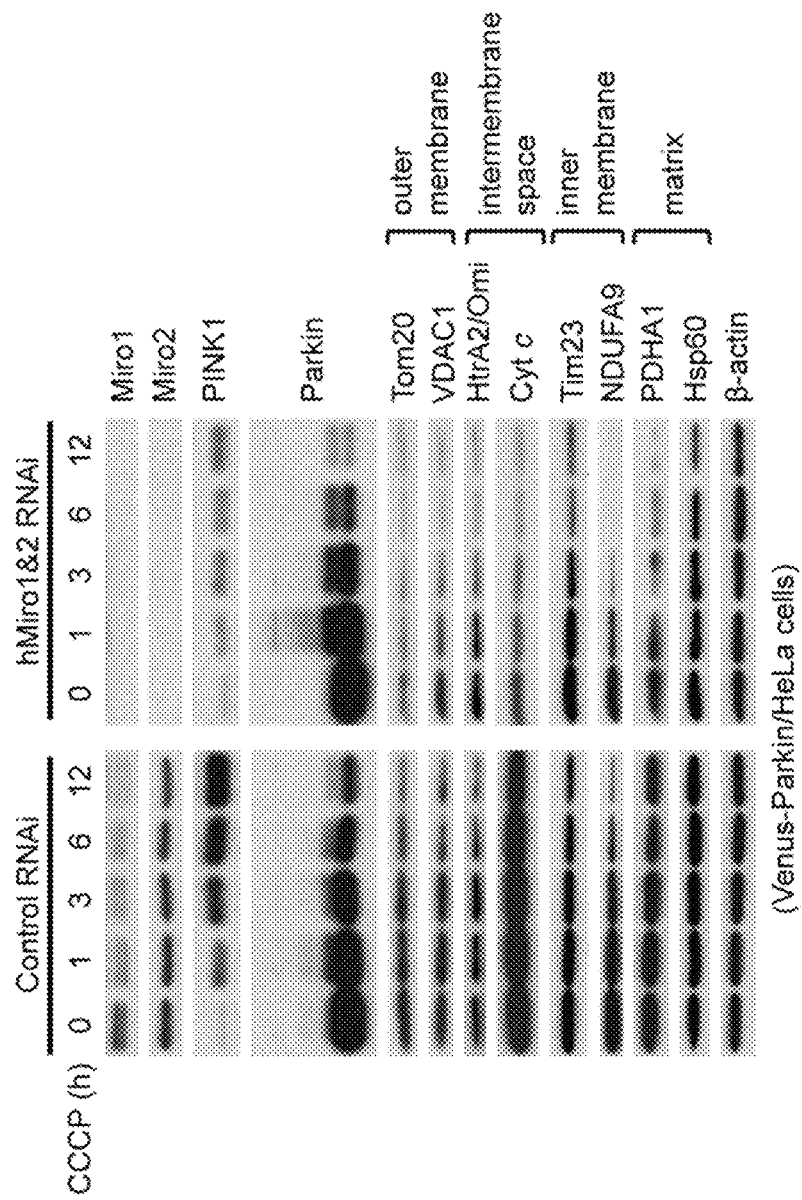
FIG. 6. Miro knockdown facilitates the removal of damaged mitochondria by Parkin-mediated mitophagy. (A) Time course of CCCP treatment to monitor mitophagy in Hela cells stably transfected with Venus-Parkin. Cells were transfected with control siRNA or hMiro1+hMiro2 siRNAs and treated with 10 µM CCCP for the indicated time. Markers for mitochondrial outer membrane (Tom20, VDAC1), intermembrane space (HtrA2/Omi, Cyt c), inner membrane (Tim23, NDUFA9), and matrix (PDHA1, Hsp60) were examined by Western blot to determine the elimination of damaged mitochondria. β-actin was used as a loading control. (B) Immunofluorescence staining showing the formation of perinuclear mitochondrial aggregates after siRNA-mediated knockdown of hMiro1 or hMiro2. HeLa cells transfected with control siRNA, hMiro1 siRNA, hMiro2 siRNA, or hMiro1+hMiro2 siRNAs were stained for Tom20 and α-tubulin. Merged images are shown to the right. Insets show enlarged view of mitochondrial morphology in the boxed areas. Arrowheads indicate ring-like or round-shaped mitochondria. (C) Miro knockdown facilitates the early stage of mitophagy in venus-Parkin transfected HeLa cells treated with CCCP. HeLa cells stably transfected with venus-Parkin were co-transfected with control siRNA or hMiro1+hMiro2 siRNAs and then treated with the DMSO vehicle or CCCP for 90 mins or 3 hrs. Venus-Parkin (blue), Tom20 (green), and Hsp60 (red) were visualized by immunostaining. Merged Tom20/Hsp60 signals are shown to the right. Cells of interest are outlined.
Figure 6C:
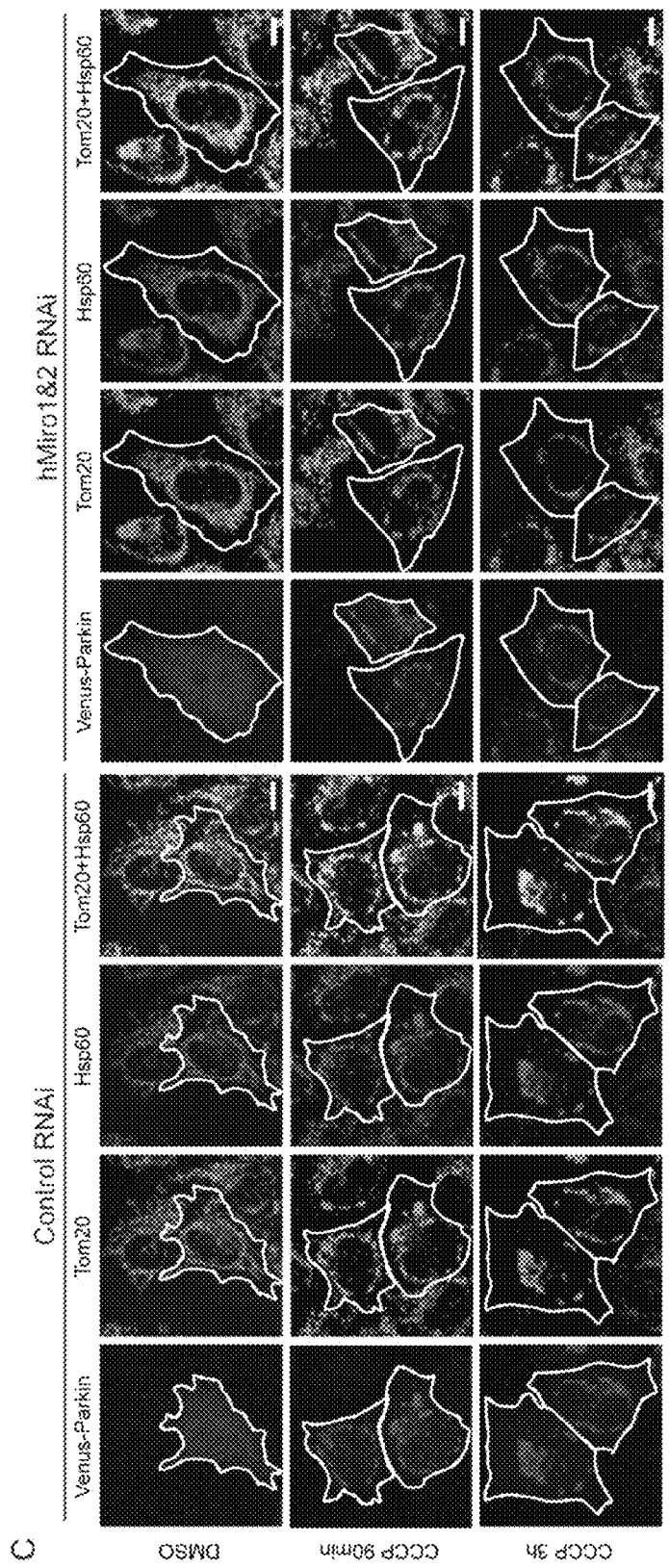

Removal of damaged or dysfunctional mitochondria through mitophagy could be one mechanism by which the PINK1/Parkin pathway maintains mitochondrial health, at least under some conditions, and the accumulation of those abnormal mitochondria in PINK1 mutants could be the underlying cause of disease pathogenesis. Consistent with this notion, it was previously shown that enhancing autophagy could efficiently rescue dPINK1 mutant phenotypes (Liu S., et al. Reduction of Protein Translation and Activation of Autophagy Protect against PINK1 Pathogenesis in Drosophila melanogaster. PLoS Genet. 2010; 6: e1001237). To better understand the rescuing effect of Miro-RNAi in PINK1 mutant background, the effect of Miro knockdown on mitophagy was examined. CCCP treatment was used to induce mitochondrial damage in HeLa cells stably transfected with venus-Parkin, and subsequently monitored the removal of damaged mitochondria over time by examining the protein levels of mitochondrial markers on the inner/outer membrane or in the matrix and inter-membrane space. Simultaneous knockdown of hMiro1 and hMiro2 significantly accelerated the mitochondrial removal process, with all the mitochondrial markers disappearing faster in hMiro knockdown cells than in the control siRNA-treated cells (FIG. 6A). This suggested that there was more active mitophagy after hMiro knockdown. To confirm this result, the mitochondrial network was monitored by immunofluorescence staining. Compared to the control siRNA-treated cells, knockdown of either hMiro1 or hMiro2 led to the accumulation of mitochondria in the perinuclear region, and knockdown of both hMiro1 and hMiro2 further enhanced this effect (FIG. 6B). Fluorescence from the immunostaining of Tom20 (an OMM marker) but not HSP60 (a matrix marker) in hMiro1 and hMiro2 double knockdown cells was noticeably weaker than that in control siRNA treated cells at 3 h after CCCP treatment (FIG. 6C), supporting the notion that hMiro knockdown facilitated an early event in Parkin-mediated mitophagy.

The Conserved Ser-156 Residue in hMiro1 is not Required for PINK1/Parkin-Mediated Degradation Under Normal or CCCP Treatment Conditions in HeLa Cells.

Figure 7A:
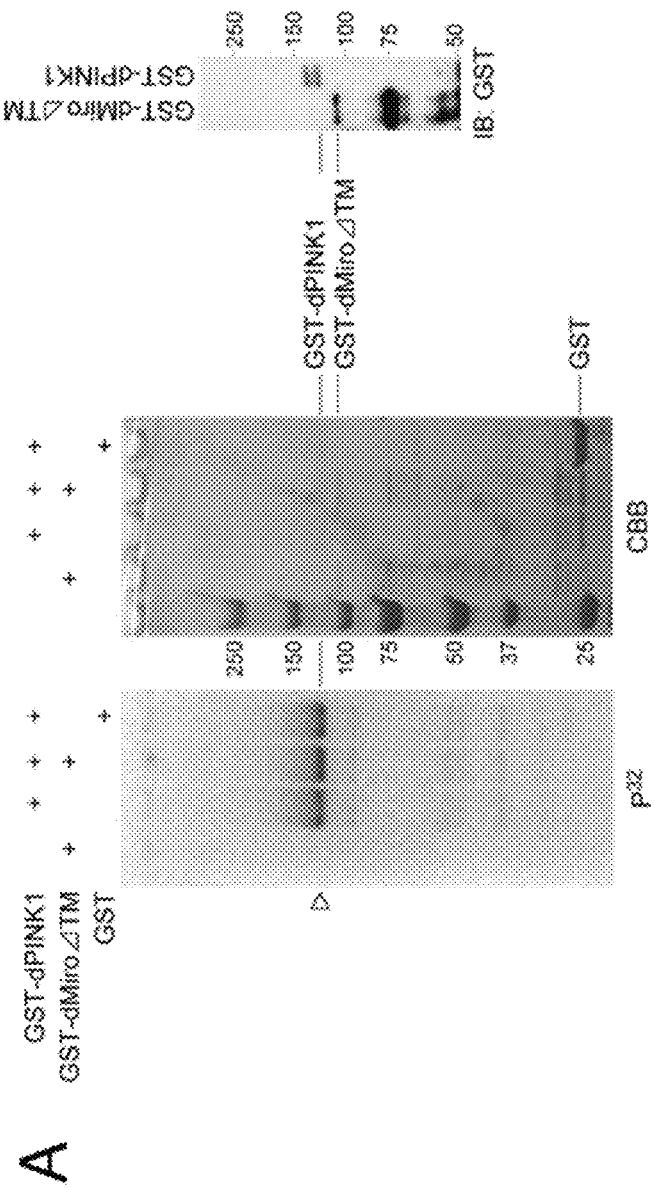
FIG. 7. Effects of PINK1 loss of function on endogenous Miro protein level in mammalian cells and testing potential direct phosphorylation of Miro by PINK1. (A) Lack of direct phosphorylation of GST-dMiroΔTM by 2×GST-dPINK1. Autoradiography ($P^{32}$) and Coomassie Brilliant Blue (CBB) staining of the same SDS-PAGE gel of the in vitro kinase reactions were shown. The presence of the GST-dMiroΔTM and 2×GST-dPINK1 proteins was further confirmed by Western blot with anti-GST. The detected $P^{32}$ signals represent PINK1 autophosphorylation. (B) Western blot analysis comparing the stability of transfected Myc-hMiro1-wild type (wt) and Myc-hMiro1-S156A in HeLa cells with or without CCCP treatment and in the presence or absence of hPINK1+hParkin co-expression. (C) Western blot analysis of HeLa cells or Venus-Parkin stably transfected HeLa cells with or without CCCP treatment under control RNAi or PINK1 RNAi conditions. (D) Western blot analysis of mouse Miro1 and Miro2 levels in wild type or PINK1 knockout (KO) MEF cells. Extracts were treated with or without lambda phosphatase before Western blot analysis. Note that whereas the signals for a control phsopho-ATF1 (p-ATF1) protein disappeared after lambda phosphatase treatment, neither Miro1 nor Miro 2 showed mobility or intensity change after the same treatment.

The molecular mechanisms by which the PINK1/Parkin pathway regulates Miro protein level or stability was further investigated. It had been previously shown that PINK1 phosphorylates Miro at a conserved S156 residue, and that this phosphorylation activates proteasomal degradation of Miro in a Parkin-dependent manner (Wang X., et al. PINK1 and Parkin Target Miro for Phosphorylation and Degradation to Arrest Mitochondrial Motility. Cell 2011; 147: 893-906). However, repeated in vitro kinase assays using an active GST-dPINK1 recombinant protein capable of efficient autophosphorylation (Imai Y., et al. The loss of PGAM5 suppresses the mitochondrial degeneration caused by inactivation of PINK1 in Drosophila. PLoS Genet. 2010; 6: e1001229) failed to show phosphorylation of GST-dMiroΔTM, a GST fusion protein of full-length dMiro with the transmembrane domain deleted (FIG. 7A). Drosophila or mammalian PINK1 protein affinity purified from HEK293 cells by immunoprecipitation also failed to phosphorylate GST-dMiroΔTM in these assays.

Figure 7B:
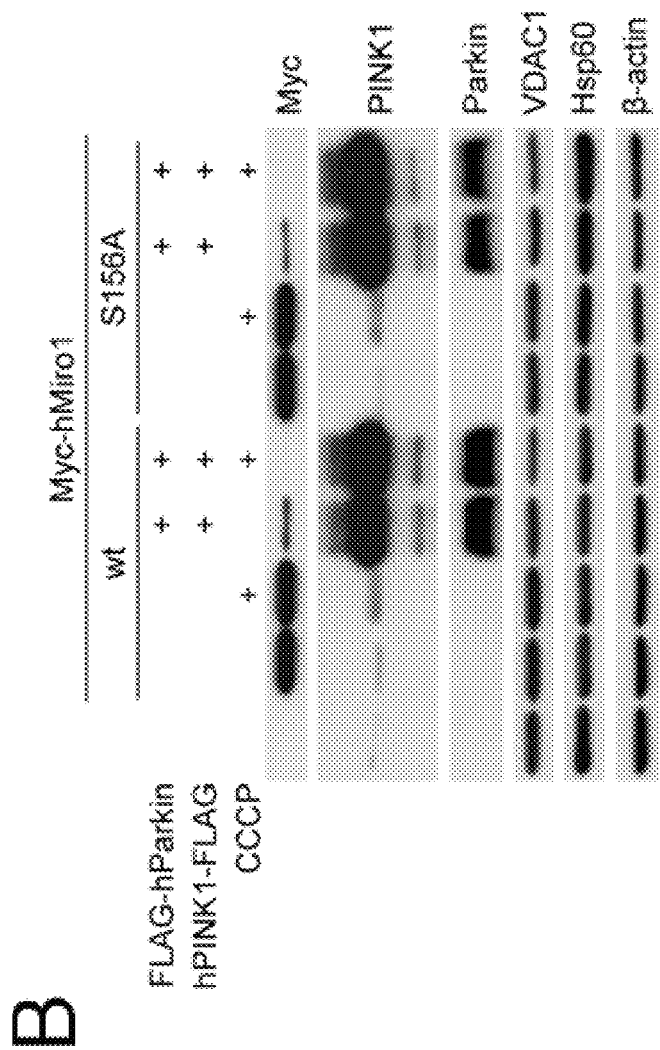

To further probe the significance of S156 phosphorylation in facilitating the proteasomal degradation of Miro promoted by the PINK1/Parkin pathway, S156A mutations were introduced into hMiro1 or hMiro2 and examined the stability of the mutant proteins in HeLa cells co-transfected with PINK1 and Parkin, under normal or CCCP treatment conditions. As shown in FIG. 7B, the wild type and S156A mutant forms of hMiro1 were equally susceptible to PINK1/Parkin-mediated degradation under both conditions. The wild type and S156A mutant forms of hMiro2 behaved similarly as well.

Effect of Loss of PINK1 Function on Miro Protein Level in Mammalian Cells.

Figure 7C:
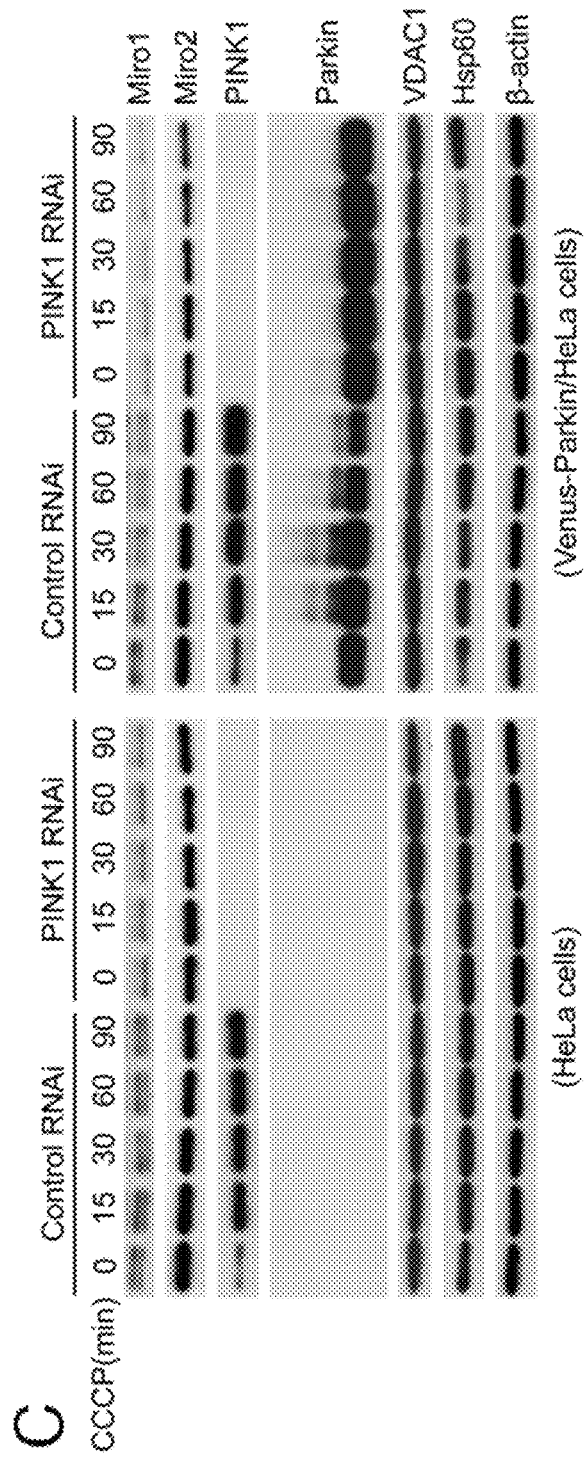
Figure 7D:
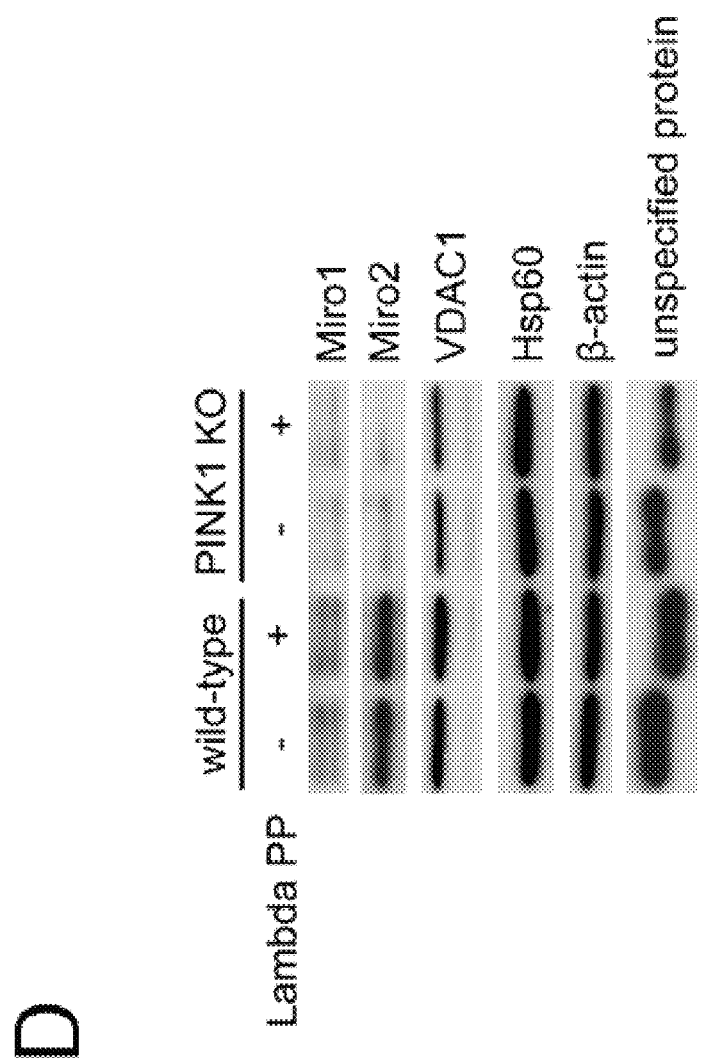
Figure 8:
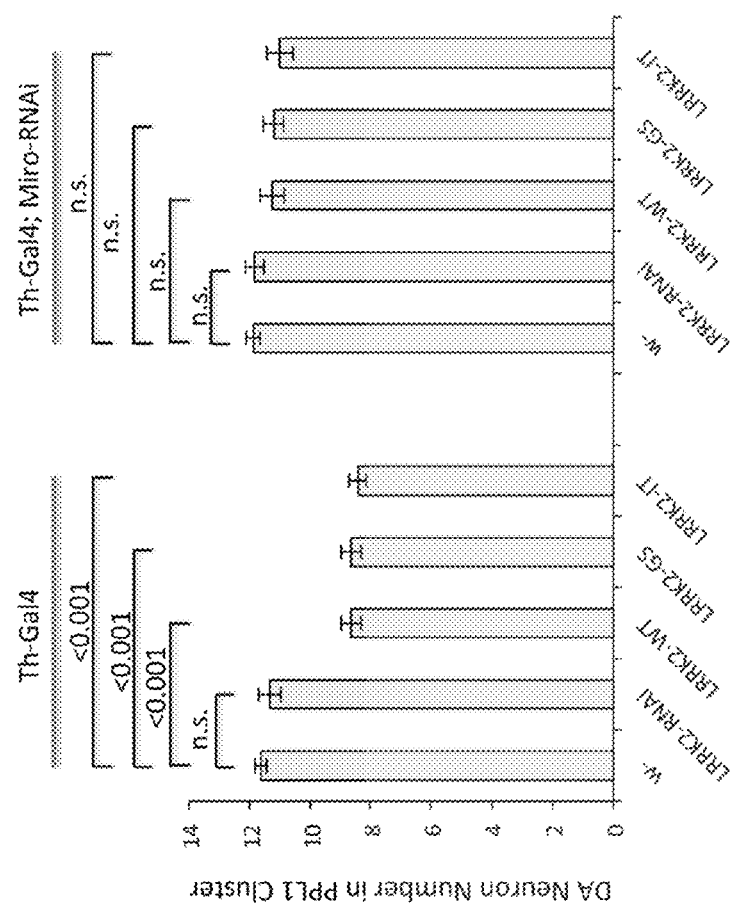
FIG. 8. DA neuron loss caused by overexpression of wild-type or mutant forms of LRRK2 can be rescued by decreasing Miro level. Mutations in LRRK2 have been associated with Parkinson's disease type 8. The Gly2019Ser (GS) and Ile2020Thr mutations in LRRK2 are relatively common causes of familial Parkinson's disease in Caucasians. They may also cause sporadic Parkinson's disease. As shown in the Figure, the DA neuron loss caused by overexpression of wild-type or mutant forms of LRRK2 can be rescued by decreasing Miro level. Flies were aged for 25 days at 29° C.

The effect of loss of PINK1 function on Miro protein level in mammalian cells was assessed. For this purpose, HeLa cells with PINK1 knockdown and MEF cells derived from PINK1 (−/−) knockout mice were used. Surprisingly, unlike the situation in *Drosophila*, endogenous Miro1 or Miro2 protein levels were significantly reduced in PINK1 RNAi cells under normal or CCCP treatment conditions (FIG. 7C, PINK1 RNAi in HeLa cells or Venus-Parkin stably transfected HeLa cells) and in PINK1 (−/−) MEF cells (FIG. 7D). The introduction of Venus-Parkin resulted in CCCP/PINK1-dependent degradation of Miro1 (FIG. 7C, Control RNAi in Venus-Parkin transfected HeLa cells). Thus, loss of PINK1 function in mammalian cells can lead to reduced expression of Miro1 and Miro2 proteins, presumably through mechanisms distinct from that operating under PINK1/Parkin co-overexpression condition.

Discussion

Mitochondrial dysfunction has long been implicated in the pathogenesis of PD. However, the exact mechanisms by which mitochondrial dysfunction arises in the disease process and how cells, particularly neurons, handle dysfunctional mitochondrial are not well understood. The identification of a mitochondrial quality control system involving two familial PD genes, PINK1 and Parkin, has provided a much-needed point of entry to elucidate the role of mitochondria in the pathogenesis of PD. These results presented herein showed that PINK1 directly regulates mitochondrial transport and that it affects the stability and/or activity of Miro, a mitochondrial Rho GTPase with a well-establish function in mitochondrial transport. This conclusion is supported by the following evidence: 1) dMiro protein level is negatively regulated by PINK1 and Parkin in vivo in *Drosophila*; 2) overexpressed PINK1 and Parkin act together to promote the ubiquitination and degradation of hMiro1 in HeLa cells; 3) reduction of the activities of Miro or other components of the mitochondrial transport machinery effectively rescued dPINK1 mutant phenotypes; 4) overexpression of dMiro in DA neurons phenocopied dPINK1 loss-of-function effects; 5) manipulation of dPINK1 activity produced clear mitochondrial motility phenotypes opposite to that observed for dMiro manipulation in *Drosophila* larval motor neurons. Together, these results support that the mitochondrial transport defects caused by PINK1 inactivation represent one of the key pathogenic events that contribute to PD pathogenesis in the *Drosophila* model.

The results provided herein offer new insights into the mode of action of the PINK1/Parkin pathway in mitochondria quality control. It was shown that, in *Drosophila* models, PINK1 OE led to decreased mitochondrial flux and net velocity, as observed in Miro knockdown background. In addition, it was found that Miro knockdown could facilitate an early step of mitophagy in mammalian cells. These observations, together with the finding that the normally labile PINK1 protein is stabilized on damaged mitochondria (Narendra D. P., et al. PINK1 Is Selectively Stabilized on Impaired Mitochondria to Activate Parkin. PLoS Biol. 2010; 8: e1000298), teach a scenario whereby the accumulation of PINK1 on damaged mitochondria and the subsequent turnover of Miro could exert neuroprotection by (1) preventing damaged mitochondria from being anterogradely transported along the axons, thus increasing their chance of getting eliminated in the soma; and (2) promoting elimination of damaged mitochondria through mitophagy. This explains the normal protective function of PINK1. When PINK1 function is impaired, however, on one hand mitochondria become dysfunctional as evidenced by morphology changes and impaired electron transport chain function (Park J., Lee, et al. Mitochondrial dysfunction in *Drosophila* PINK1 mutants is complemented by parkin. Nature. 2006; 441: 1157-1161; Clark I. E., et al. *Drosophila* pink1 is required for mitochondrial function and interacts genetically with parkin. Nature. 2006; 441: 1162-1166; Yang Y., et al. Mitochondrial pathology and muscle and dopaminergic neuron degeneration caused by inactivation of *Drosophila* Pink1 is rescued by Parkin. Proc Natl Acad Sci USA. 2006; 103: 10793-10798; Liu W., et al. Pink1 regulates the oxidative phosphorylation machinery via mitochondrial fission. Proc Natl Acad Sci USA. 2011; 108: 12920-12924; Gautier C. A., et al. Loss of PINK1 causes mitochondrial functional defects and increased sensitivity to oxidative stress. Proc Natl Acad Sci USA. 2008; 105: 11364-11369; Sato S., et al. Genetic mutations and mitochondrial toxins shed new light on the pathogenesis of Parkinson's disease. Parkinsons Dis. 2011; 2011: 979231; Exner N., et al. Loss-of-function of human PINK1 results in mitochondrial pathology and can be rescued by parkin. J. Neurosci. 2007; 27: 12413-12418), while on the other hand, as shown in this study in *Drosophila* models, the anterograde mitochondrial transport is enhanced. As a result, the dysfunctional mitochondria would have increased retention in the axons and synapses, resulting in increased reactive oxygen species (ROS) production, oxidative damage, and subsequent synaptic and axonal degeneration and eventual neuronal loss.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating mitochondrial disease in a subject having a mitochondrial disease, comprising
administering a therapeutically effective amount of an inhibitor of a mitochondrial transport protein to the subject, wherein the administering stabilizes or reduces an undesirable clinical symptom in the subject.

2. The method according to claim 1, wherein the mitochondrial transport protein is a Miro protein.

3. The method according to claim 1, wherein the mitochondrial transport protein is a trafficking kinesin (TRAK) protein.

4. The method according to claim 1, wherein the mitochondrial transport protein is kinesin heavy chain (Khc).

5. The method according to claim 1, wherein the inhibitor is a nucleic acid.

6. The method according to claim 1, wherein the mitochondrial disease is Parkinson's disease.

7. The method according to claim 6, wherein the Parkinson's disease is a PTEN-induced putative kinase 1 (PINK-1)-associated form of PD.

8. The method according to claim 6, wherein the inhibitor is administered to the midbrain and/or putamen of the subject.

9. The method according to claim 6, further comprising the step of administering to the individual a therapeutically effective amount of one or more agents selected from the group consisting of levodopa, a dopamine agonist, a MAO-B inhibitor, amantadine, or an anticholinergic prior to, concurrently with, or after administering the inhibitor of a mitochondrial transport protein.

10. A method of treating Parkinson's disease in a subject having Parkinson's disease, comprising:
administering a therapeutically effective amount of an inhibitor of a Miro protein to the subject having Parkinson's disease (PD), wherein the administering stabilizes or reduces an undesirable clinical symptom in the subject,
wherein the Parkinson's disease is a PTEN-induced putative kinase 1 (PINK-1)-associated form of PD.

11. The method according to claim 10, wherein the inhibitor is a nucleic acid.

12. The method according to claim 10, wherein the inhibitor is administered to the midbrain and/or putamen of the subject.

* * * * *

SEQUENCE LISTING

```
<160> NUMBER OF SEQ ID NOS: 6

<210> SEQ ID NO 1
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 1
cgcccgggtg agcagaaact catctctgaa gaag                              34

<210> SEQ ID NO 2
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 2
atgcggccgc tacttggggt cctccgtcat c                                 31

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 3
gcagagctct tttattacgc ac                                           22

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
tatgttcttc aggttttcg c                                             21

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
gcagagctgt tctactacgc                                              20

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
gatgttcctc aggttcttgg c                                            21
```